United States Patent [19]
Schwarz et al.

[11] Patent Number: 5,723,119
[45] Date of Patent: Mar. 3, 1998

[54] METHOD FOR ENHANCING WOUND HEALING/REPAIR WITH IL-4

[75] Inventors: Martin A. Schwarz, Verona; Lee M. Sullivan, Edison; Loretta A. Bober, Linden; Michael J. Grace, Hamilton Township, all of N.J.

[73] Assignee: Schering Corporation, Kenilworth, N.J.

[21] Appl. No.: 451,112

[22] Filed: May 25, 1995

Related U.S. Application Data

[63] Continuation of Ser. No. 344,323, Nov. 23, 1994, abandoned, which is a continuation of Ser. No. 835,891, Feb. 14, 1992, which is a continuation-in-part of Ser. No. 386,937, Jul. 28, 1989, abandoned, and Ser. No. 639,631, Jan. 10, 1991, abandoned.

[51] Int. Cl.$^6$ .................................................. A61K 00/00
[52] U.S. Cl. .................. 424/85.2; 424/85.1; 514/2; 514/8; 514/12
[58] Field of Search .................. 424/85.1, 85.2; 514/2, 8, 12

[56] References Cited

FOREIGN PATENT DOCUMENTS 9011301  10/1990  WIPO.
9101744   2/1991  WIPO.

OTHER PUBLICATIONS

Kapp et al, *J. Invest Dermatol* 95(6) 1990, pp. 945–995.
Ford et al, *Arch Surg* 124, 1989, pp. 1422–1428.
Ten Dijke et al, *Bio/Technology* 7, 1989, pp. 793–798.
Brunt, *Bio/Technology* 7, 1989, pp. 15–16.
Carrico et al, *Surgical Clinical of North America* 64(4) 1984, pp. 721–733.
Luger et al, *J. Am. Acad. Derm. et al* 24(6) 1991 pp. 915–926.
Zeck-Kapp et al, Immunobiology 179(1) 1989, pp. 44–55.
J. Cell. Biochem. Keystone Symposium on Wound Healing Apr. 1991 pg vary.
Arai et al, J. Immunol. 142:274 (1989).
Defrance et al, J. Exp. Med. 165:1459 (1987).
Grabstein et al, J. Exp. Med. 163:1405 (1986).
Howard et al, J. Exp. Med. 155:914 (1982).
Lee et al, Proc. Natl. Acad. Sci. USA 83:2061 (1986).
Monroe et al, Clinical Immunol. Immunopath. 49:292 (1988).
Otsuka et al, Nucleic Acids Res. 15:333 (1987).
Pene et al, Proc. Natl. Sci. USA 85:6880 (1988).
Peschel et al, J. Immunol 142:1558 (1989).
Thornton et al J. Leukocyte Biol. 47:312 (1990).
Trenn et al, J. Immunol. 140:1101 (1988).
Yokota et al, Proc. Natl. Acad. Sci. USA 83:5894 (1986).

*Primary Examiner*—Garnette D. Draper
*Attorney, Agent, or Firm*—Norman C. Dulak; Cynthia L. Foulke; Immac J. Thampoe

[57] ABSTRACT

Disclosed are methods of enhancing the reparative phase of wound healing and repair in a mammal by administering to the wound site during the reparative phase an effective amount of IL-4. Also disclosed are methods of enhancing the healing and repair of infected wounds, wounds of diabetic mammals, and wounds of immunocompromised mammals by administering a therapeutically effective amount of IL-4 to the wound.

11 Claims, 15 Drawing Sheets

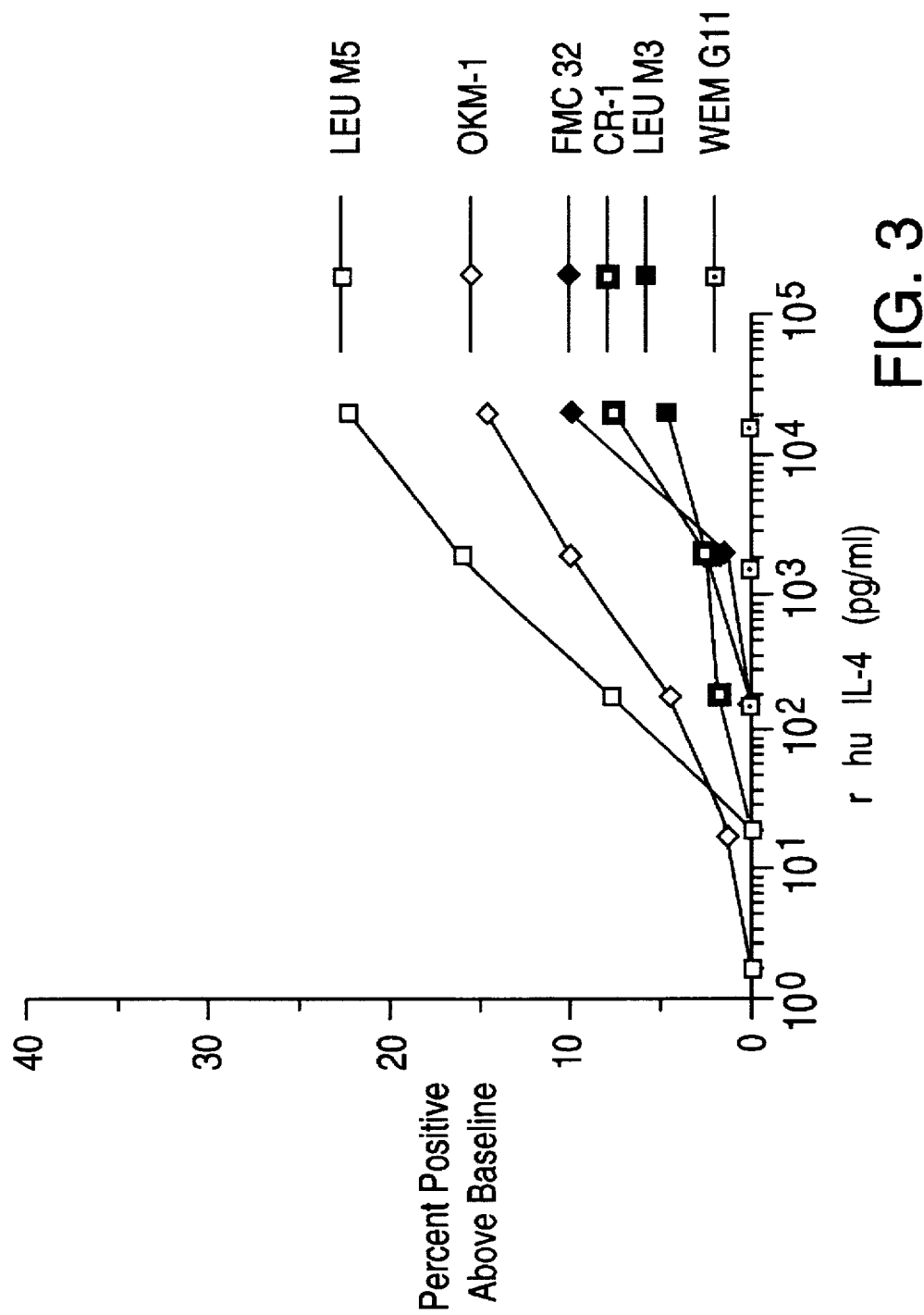

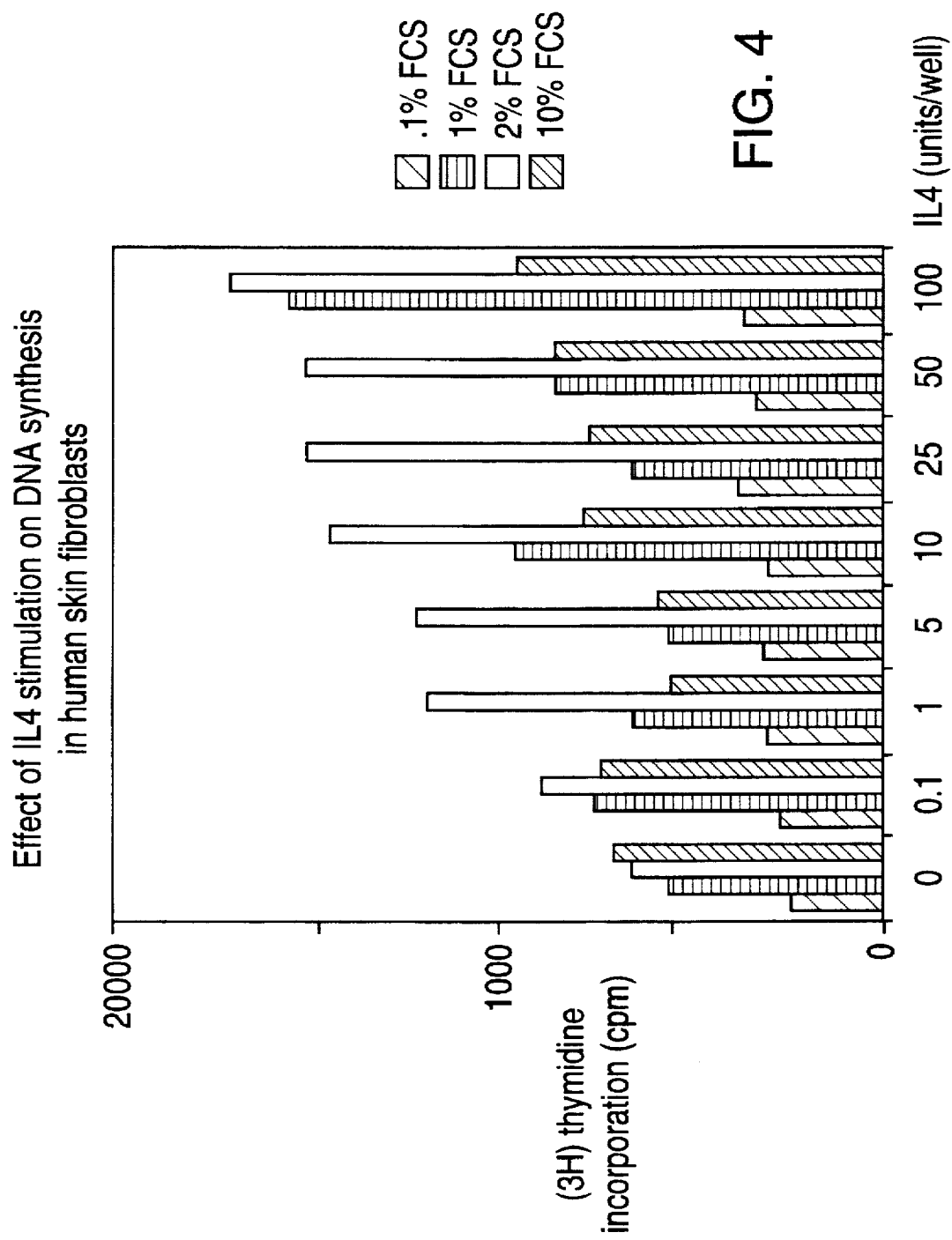

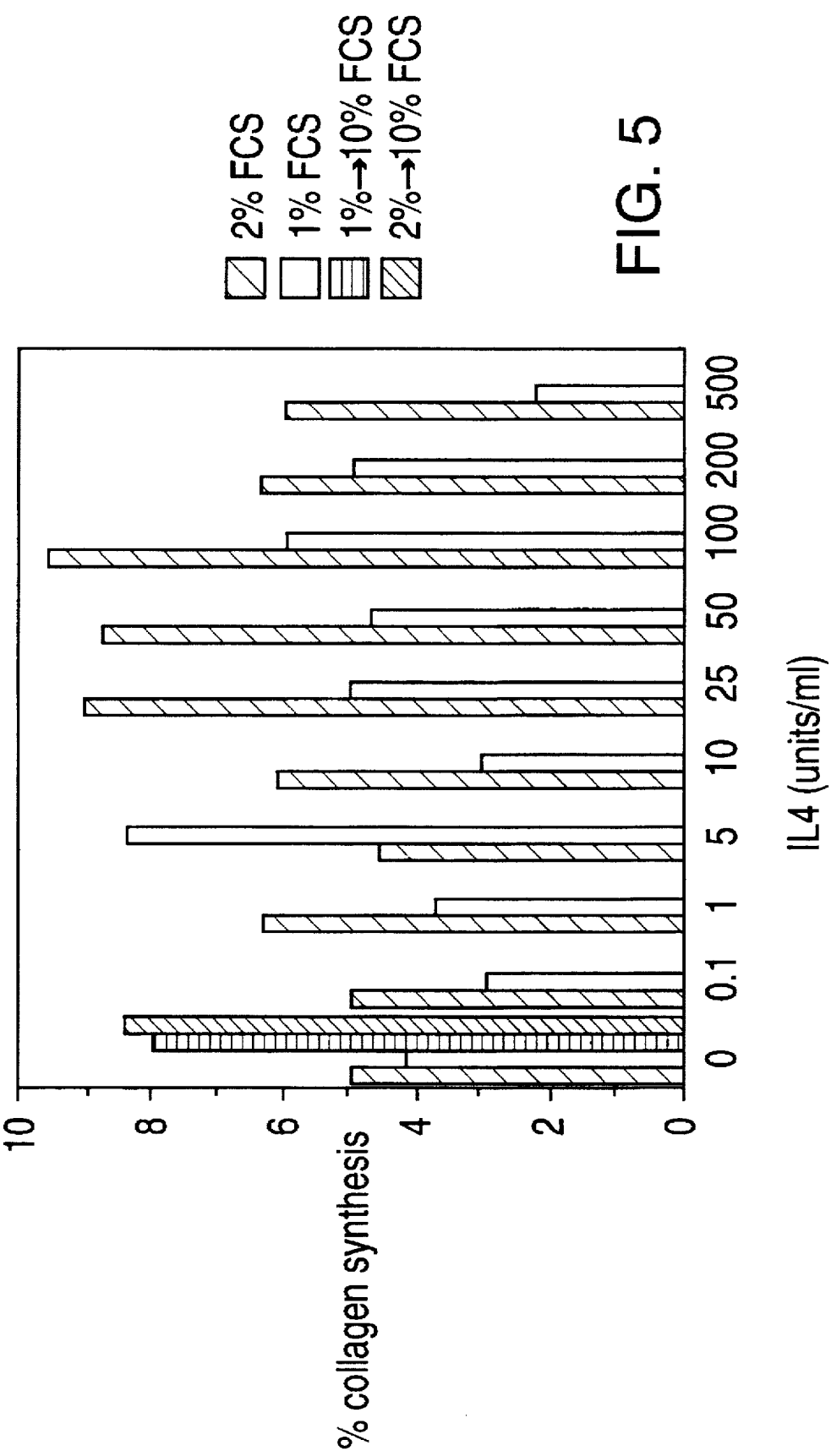

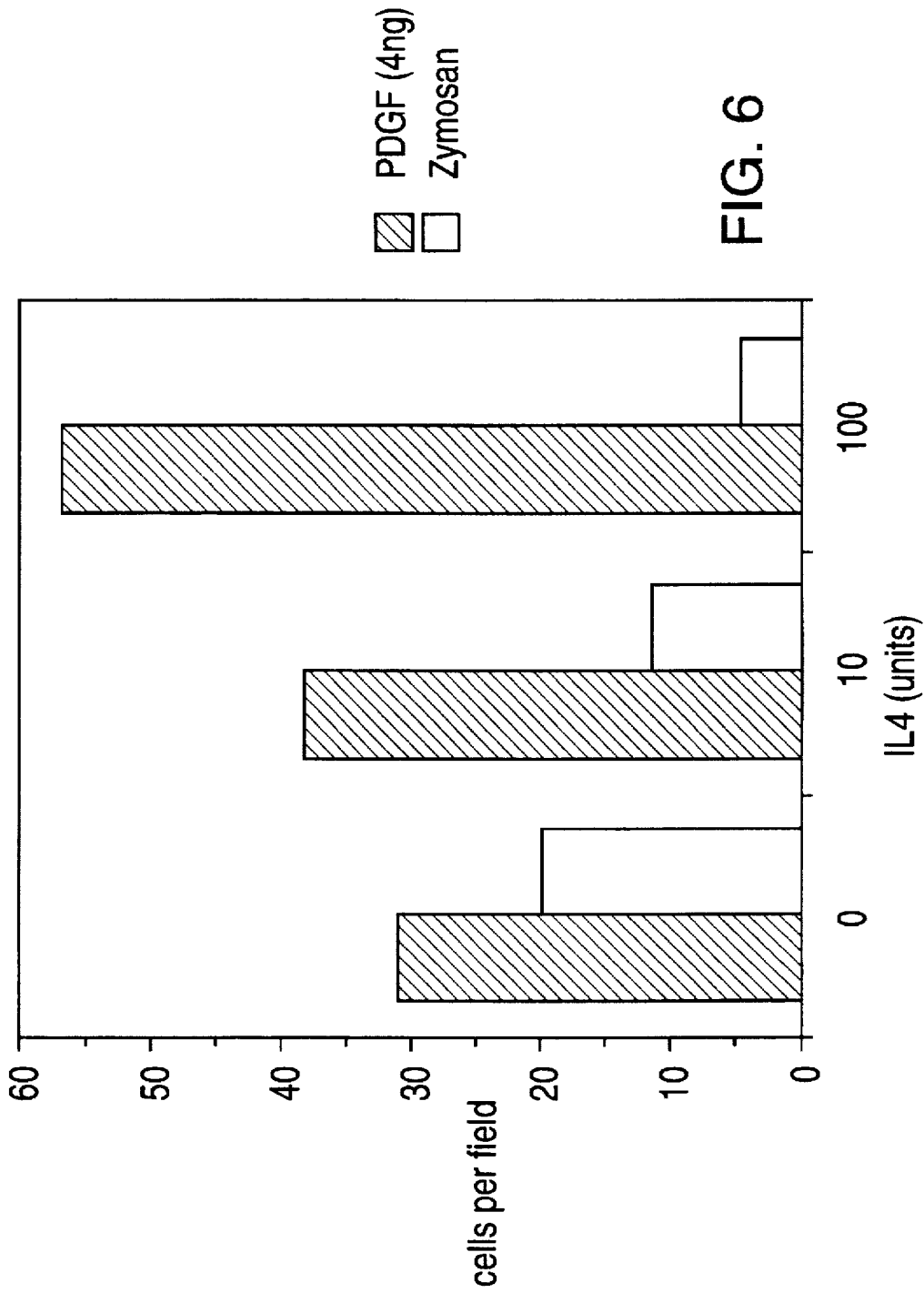

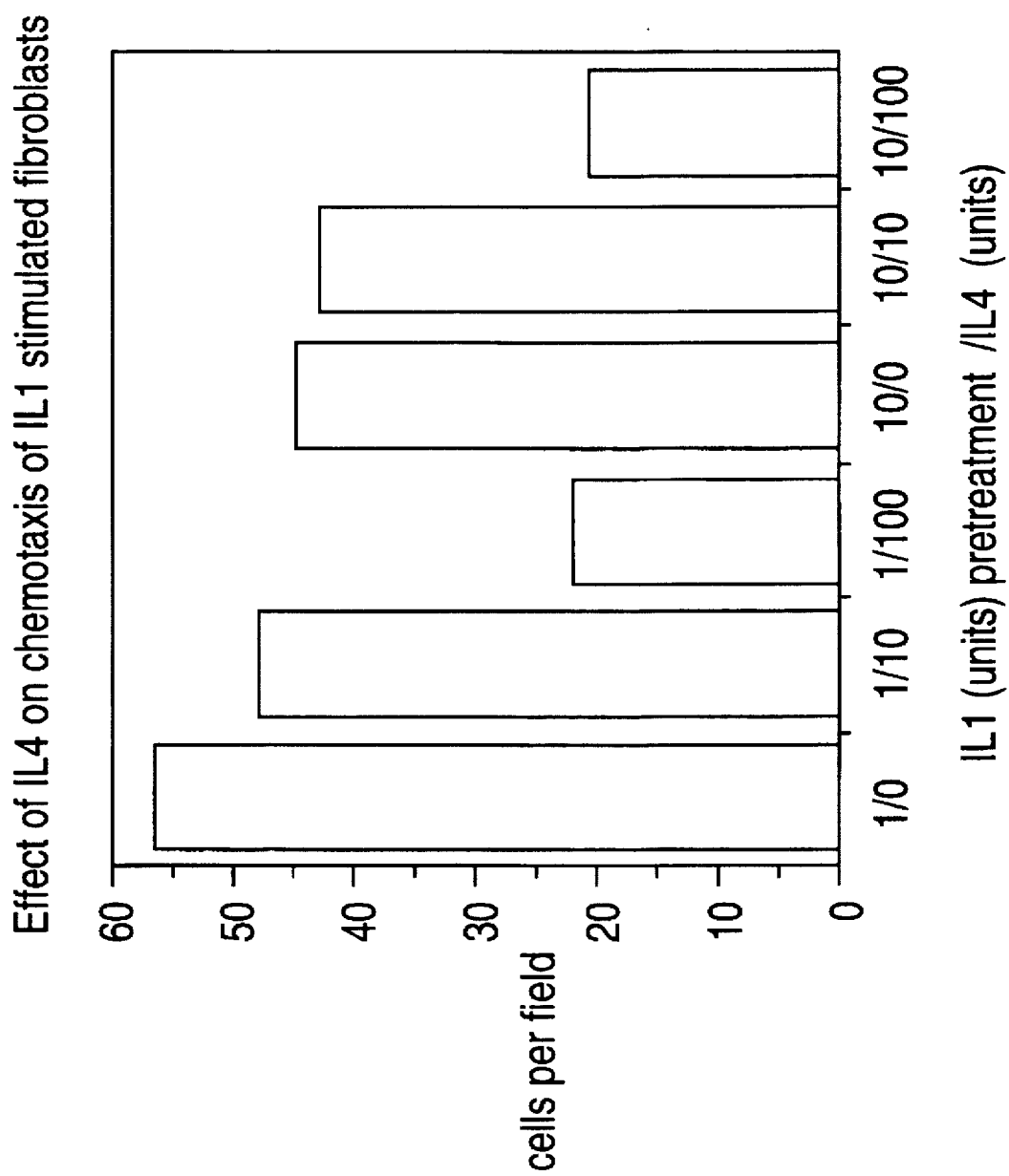

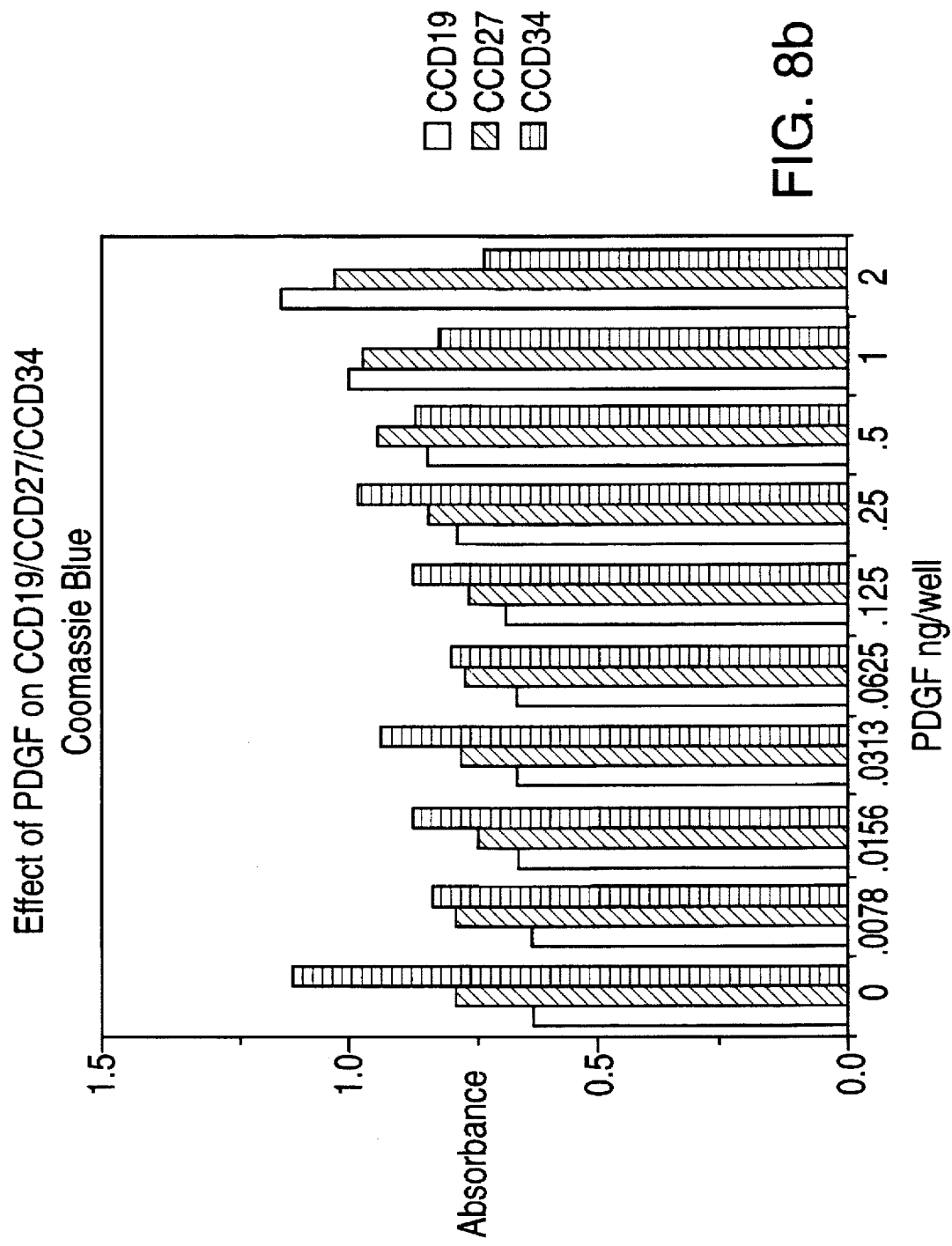

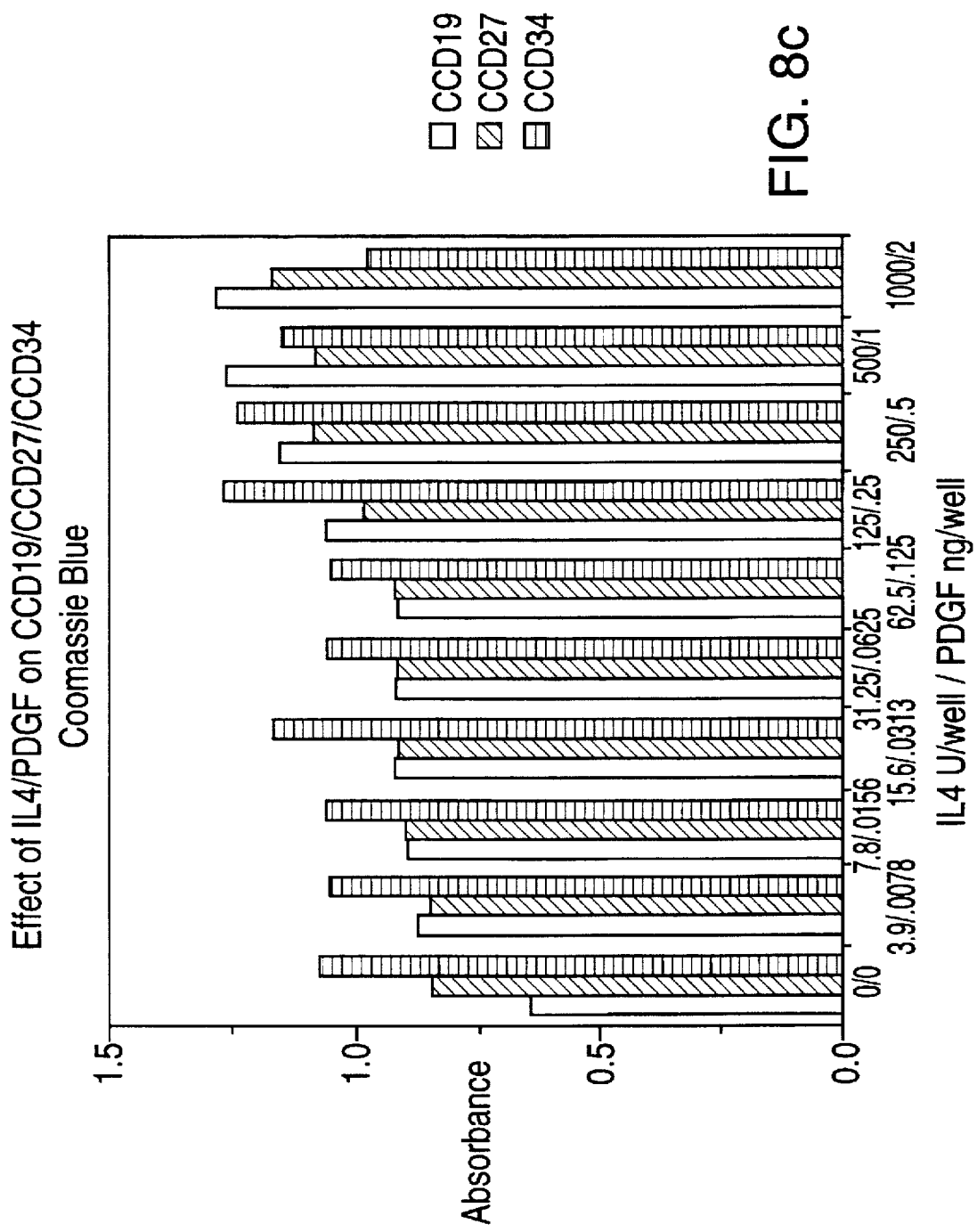

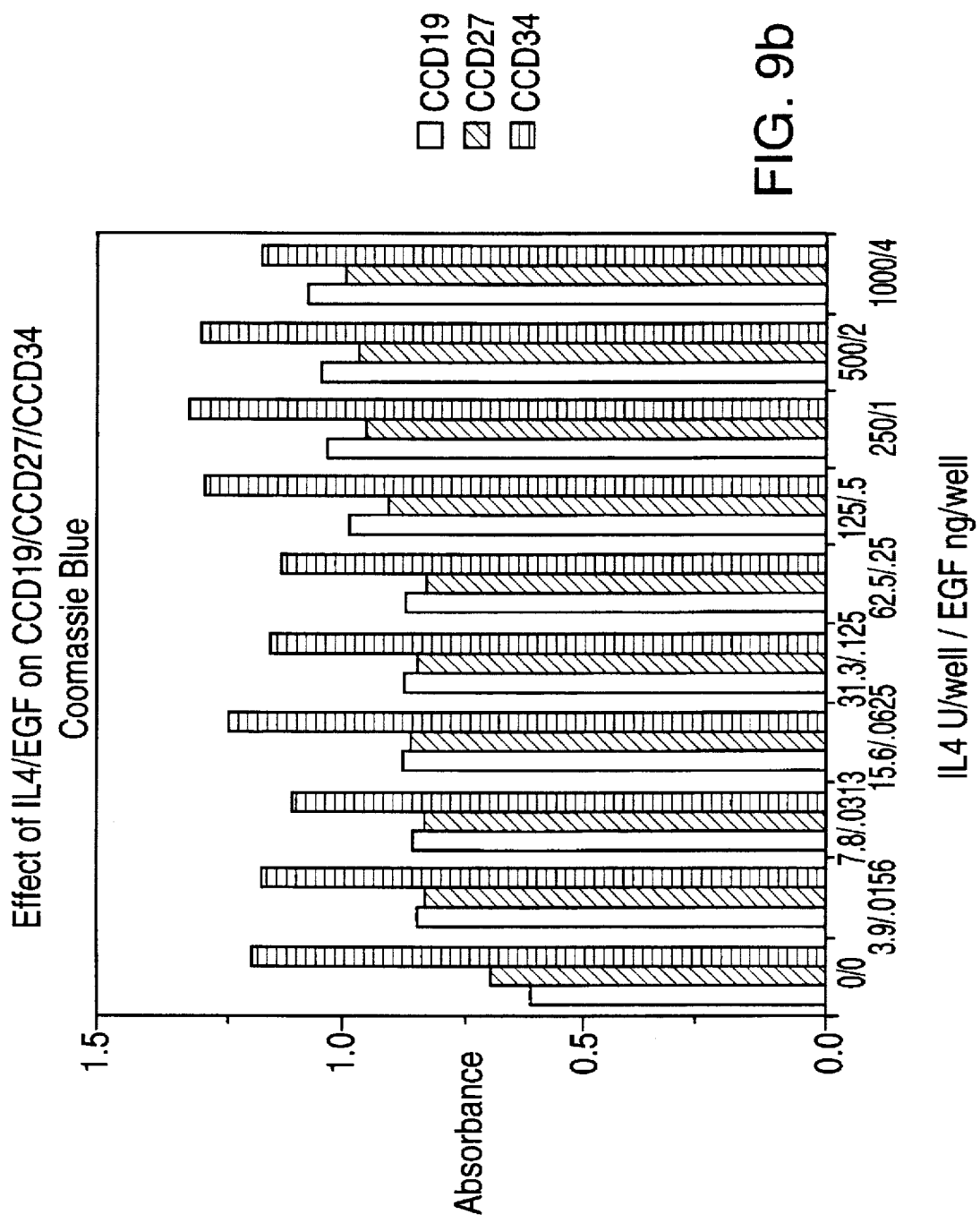

METHOD FOR ENHANCING WOUND HEALING/REPAIR WITH IL-4

This is a continuation U.S. patent application Ser. No. 08/344,323, filed Nov. 23, 1994 now abandoned which is a continuation of U.S. patent application Ser. No. 07/835,891 filed: Feb. 14, 1992 which is a continuation-in-part of U.S. patent application Ser. No. 07/386,937 filed on Jul. 28, 1989 and of U.S. patent application Ser. No. 07/639,631 filed on Jan. 10, 1991.

BACKGROUND OF THE INVENTION

Interleukin-4 (IL-4) is a lymphokine (stimulator of the immune system) that has a broad range of immune cell stimulation as described in Banchereau et al., *Lymphokine Res.* Vol. 6, No. 1: U135 (1987); Yokoto et al., *Proc. Natl. Acad. Sci. USA*, 83: 5894–5898 (1986); Lee at al., *Proc. Natl. Acad. Sci. USA*, 83: 2061–2065 (1986); Coffman et al., *J. Immunol.* 136: 949–954 (1986); Sanderson et al., *Proc. Natl. Acad. Sci. USA*, 83: 437–440 (1986); Grabstein et al., *J. Exp. Med.*, 163: 1405–1413 (1985); and Vitetta et al., *J. Exp. Med.* 162: 1726–1731 (1985). During its early development IL-4 has also been referred to as B-cell growth factor (BCGF) [Butler et al., *J. Immunol.* 133: 251–255 (1984) (human BCGF); and Farrar et al., *J. Immunol.* 131: 1838–1842 (1983)(mouse BCGF)] and B-cell stimulatory factor 1 (BSF-1) [Ohara et al., *J. Immunol.* 135: 2518–2523 (1985)]. The clarification and designation of the name interleukin-4 was finally proposed and adopted in 1986 [Sanderson et al., *Proc. Natl. Acad. Sci. USA*, 83: 437–440 (1986)].

IL-4 was originally thought to be important only for the co-stimulation of activated B cells, Roehm, et al., Interleukin Induced Increase In Ia Antigen Expression By Normal B. Cells, *J. Exp. Med.*, 160:679–6 1984. It has also been shown to modulate the activities of T cells and cells, Mosmann, et al., T cell and mast cell lines respond to B cell stimulatory factor-1, *Proc. natl. Acad. Sci. USA.*, 83:5654–5658, 1986. also WO 87/0290 where IL-4's activity as a T-cell growth factor and B-c growth factor is described as being useful to enhance natural defense against various infections.

T-cells and B-cells usually act in the later stages of an immune response. It would be highly advantageous to have an agent which would increase and activate neutrophils which act in the early stages of infection and are the body's first line of defense against infection.

In the normal process of white blood cell hematopoiesis, cells originate in the bone marrow from a primitive immature cell known as a stem cell and differentiate through progressively more mature stages along different lineage pathways to arrive at a terminal state of differentiation as a monocyte, granulocyte or lymphocyte.

A property of immature, undifferentiated cells is the ability to multiply rapidly. It is only when a precursor cell matures and differentiates through these multiple stages that they generally lose their capacity to proliferate and assume the role of a specialized, functional mature cell. In the normal state, cells that reach their final mature form do not proliferate to any great extent, if at all.

In general cancer is a disorder of cell differentiation. In particular myeloid leukemias are disorders in which cells of monocytic and granulocytic lineages are blocked at an early stage of maturation and thus have not lost their proliferative capacity. These maturation arrested cells continue to proliferate, and give rise to a population of immature cancer cells resulting in a diagnosis of leukemia.

There is evidence that various myeloid leukemia cells can be induced to differentiate into normal macrophages and granulocytes and that upon differentiation these cells lose their capacity to proliferate. This suggests that the induction of terminal differentiation by an agent would have usefulness as a therapy for myeloid leukemia.

SUMMARY OF THE INVENTION

We have now surprisingly found that administration of IL-4 increases the neutrophil count in mammals and stimulates differentiation and activation of neutrophils and monocytes. Even more surprisingly, we have found that the increase in and activation of neutrophils continues long after dosing with IL-4 has been terminated. This is very surprising since the half-life of IL-4 in the body is very short. We have thus discovered that IL-4 may be administered to a mammal to increase and activate neutrophils and provide increased host resistance to infection or to treat infection at a very early stage. The mammal may be an immunocompromised host, e.g., any host susceptible to unwanted bacterial infection such as a patient having severe burns or ulcers, a host whose immune defenses are lowered because of radiation or chemotherapy in the treatment of cancer, and a host with a genetic immunodeficiency.

We have also discovered that IL-4 induces the maturation of myeloid and monocytoid cells. Thus, since myeloid leukemia is associated with the proliferation of immature myeloid cells, IL-4 by progressing myeloid cells to their mature state should reduce their proliferation and provide a method for treating myeloid leukemia.

Preferably, a human will be treated with IL-4 derived from a human source, i.e., human IL-4 such as human IL-4 produced recombinantly from *E. coli* or CHO cells. Most preferably, the dosage for the mammals will be administered by subcutaneous intravenous injection or intravenous infusion and will be in an amount of about 0.1 to about 30 micrograms (µgs) of IL-4 per kilogram of body weight per day. Preferably, the IL-4 is administered in an amount of about 1 to about 15 µgs of IL-4 per kilogram of body weight per day, and most preferably about 3 to about 10 µgs of IL-4 per kilogram of body weight per day.

We have also discovered that surprisingly IL-4 can stimulate DNA synthesis in human skin fibroblast cell lines. We have also discovered that, unlike known growth factors such as PDGF and epidermal growth factor (EGF), IL-4 does not stimulate significant increases in cell number in vitro. Accordingly, the present invention provides a method of enhancing the reparative phase of wound healing and repair in a mammal in need of such enhancing which comprises administering during the reparative phase of wound healing and repair an amount of IL-4 effective for such enhancing.

The present invention also provides for a method of enhancing the healing and repair of an infected wound of a mammal, especially a human being, comprising administering to the infected wound a therapeutically effective amount of IL-4.

The present invention also provides for a method of enhancing the healing and repair of a wound of a mammal afflicted with diabetes mellitus comprising administering to the wound of the mammal having diabetes mellitus a therapeutically effective amount of IL-4.

BRIEF DESCRIPTION OF THE DRAWINGS

FIG. 3 is a graphical representation of the results indicating activation and differentiation achieved by treatment of U-937 cells with IL-4.

FIG. 4 is a graphic representation of the dose dependent increase in DNA synthesis in human skin fibroblast cells incubated with IL-4 in accordance with this invention.

FIG. 5 is a graphic representation showing dose dependent increase in collagen synthesis in human skin fibroblast cells incubated with IL-4 in accordance with this invention.

FIG. 6 is a graphic representation showing IL-4 enhanced chemotaxis of human skin fibroblast cells toward PDGF in accordance with this invention.

FIG. 7 is a graphic representation of results indicating the ability of IL-4 to cause a decrease in IL-1-stimulated migration of human skin fibroblast cells toward PDGF and zymosan in accordance with this invention.

FIG. 8b is a graphic representation of the effect of PDGF on the growth of human skin fibroblast and lung cells.

FIG. 8c is a graphic representation of the IL-4 dose-dependent enhancement of the stimulation by PDGF of the growth of human skin (but not lung) fibroblast cells in accordance with this invention.

FIG. 9b is a graphic representation of the IL-4 dose-dependent enhancement of the stimulation by EGF of human skin (but not lung) fibroblast cells in accordance with this invention.

DETAILED DESCRIPTION OF THE INVENTION

Figure 1:
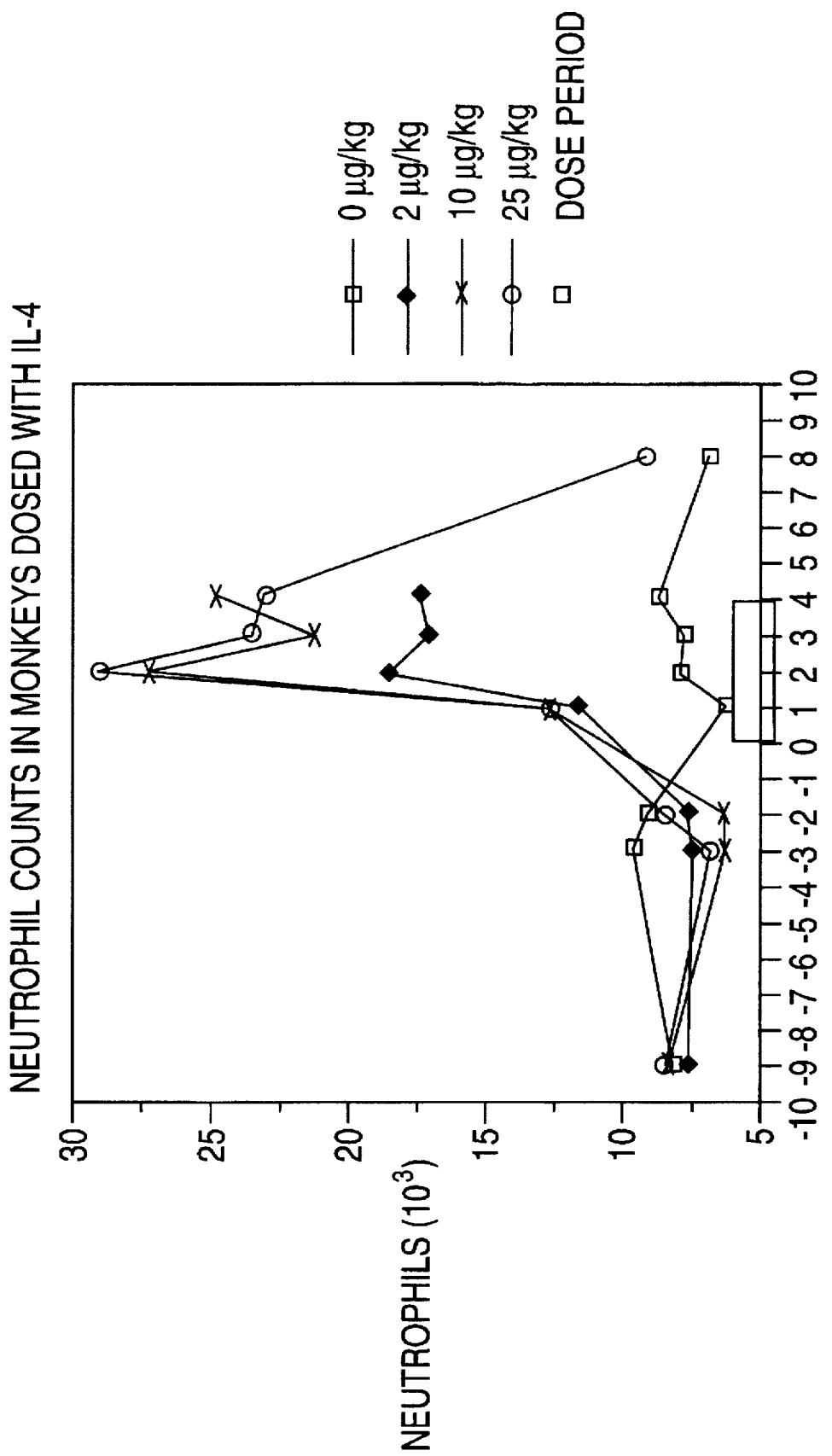
FIG. 1 is graphic representation of the increase in neutrophil cell count found by dosing Cynomolgus monkeys with IL-4.
Figure 2:
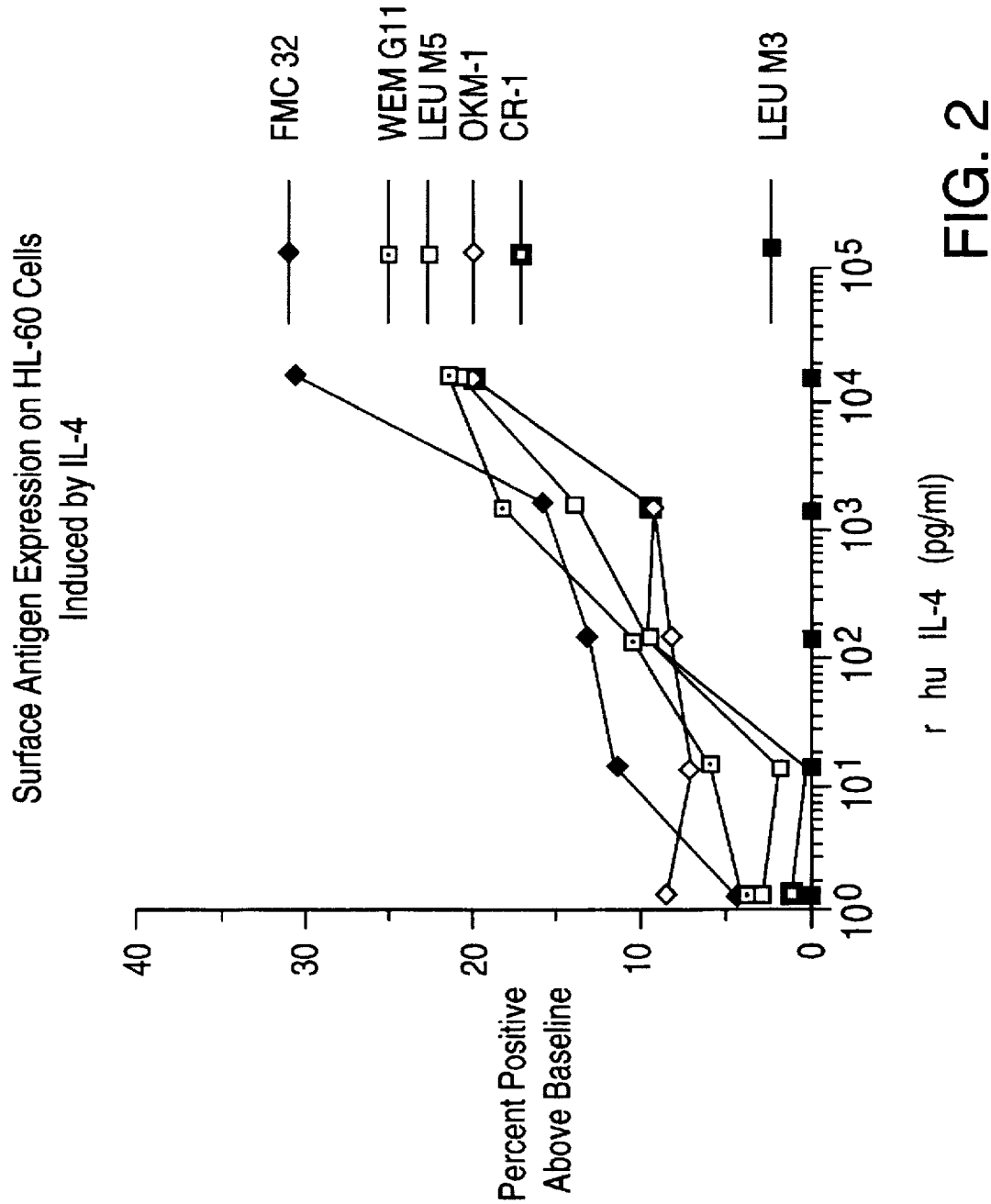
FIG. 2 is a graphical representation of the results indicating activation and differentiation achieved by treatment of HL-60 cells with IL-4.

Any suitable IL-4 may be employed in the present invention. Complementary DNAs (cDNAs) for IL-4 have recently been cloned and sequenced by a number of laboratories, e.g. Yokoto et al., *Proc. Natl. Acad. Sci. USA*, 83: 5894–5898 (1986) (human); Lee at al., *Proc. Natl. Acad. Sci. USA*, 83: 2061–2065 (1986)(mouse); Noma et al., *Nature* 319: 640–646 (1986)(mouse); and Genzyme Corporation, Boston, Mass. (human and mouse). Moreover, non-recombinant IL-4 has been purified from various culture supernatants, e.g. Sanderson et al., *Proc. Natl. Acad. Sci. USA*, 83: 437–440 (1986)(mouse); Grabstein et al., *J. Exp. Med.*, 163: 1405–1413 (1985)(mouse); Ohara et al., *J. Immunol.*, 135: 2518–2523 (1985)(mouse BSF-1); Butler et al., *J. Immunol.*, 133: 251–255 (1984)(human BCGF); and Farrar et al., *J. Immunol.*, 131: 1838–1842 (1983)(mouse BCGF). The disclosures of all the above articles are incorporated herein by reference for their teachings of DNA and amino acid sequences and of methods of obtaining suitable IL-4 materials for use in the present invention.

Preferably, the IL-4 used in the present invention will be a human IL-4, and most preferably it will be the human version with the sequence described in Yokoto et al., *Proc. Natl. Acad. Sci. USA*, 83: 5894–5898 (1986) and PCT Patent Application No. 87/02990 published May 21, 1987 that is expressed in and isolated from *E. coli* (U.S. patent application Ser. No. 079,666, filed Jul. 29, 1987 and U.S. patent application Ser. No. 194,799, filed Jul. 12, 1988) and U.S. Pat. No. 5,017,691. The disclosures of the above article, PCT Application and U.S. patent applications are hereby incorporated herein by reference.

According to this invention, mammals are administered an effective amount of an IL-4 to increase monocytes and/or granulocytes (which might be any of all of the following: polymorphonuclear cells, eosinophils and/or basophils). Such an effective amount is defined as any amount of IL-4 that will significantly increase the neutrephil count, with an increased count of at least 25 percent, preferably 50%, considered significant. From about 0.1 to about 15 micrograms of IL-4, preferably human IL-4 (hIL-4), per kilogram of body weight per day is preferably administered. More preferably, mammals are administered about 1.0 to about 10.0 micrograms of hIL-4 per kilogram of body weight per day, and most preferably mammals are administered about 1 microgram of hIL-4 per kilogram of body weight per day.

The amount, frequency and period of administration will vary depending upon factors such as the level of the neutrophil and monocyte count (e.g., the severity of the monocytopenia or granulocytopenia), age of the patient, nutrition, etc. Usually, the administration will be daily initially and it may continue periodically during the patient's lifetime. Dosage amount and frequency may be determined during initial screenings of neutrophil count and the magnitude of the effect of IL-4 upon the increase in neutrophil count. Dosage will be aimed to increase the neutrophil count to an acceptable level of about 1000 total neutrophils and/or 100 total monocytes to generate the desired biological effect, which will need to be determined individually for each patient depending on clinical circumstance. Additionally, selective manipulations may be performed, such as the enhancement of one or more subpopulations of lymphocytes.

To complement the neutrophil increasing effect of the IL-4, it may be useful to administer it in conjunction with other biologically and/or pharmaceutically active compounds. For example, it can be combined with other white cell increasing agents [e.g., granulocyte-macrophage colony stimulating factor (GM-CSF) and granulocyte-colony stimulating factor (G-CSF)]. It also might be useful to combine IL-4 with other interleukins, e.g. IL-1 and/or IL-3 and/or IL-7, for the purposes of increasing the total white blood cell and neutrophil count; IL-2 in combination with IL-4 may produce selective enhancement of specific and useful T-cell functions, and IL-4 in combination with IL-5 and/or IL-6 may be useful in specifically enhancing the function and/or numbers of normal and/or neoplastic B-cells. IL-4 may also be useful in increasing the utility of chemotherapeutic agents, including, but not necessarily limited to, alkylating agents, mitotic spindle poisons or antitumor antibiotics. By enhancing the number of white cells or the functional or differentiational status of specific subpopulations of cells, the efficacy of the aforementioned chemotherapeutic agents may be enhanced. The combination of an interferon, e.g. interferon gamma or alpha, with IL-4 may also be useful in increasing numbers and functions of certain white cell, particularly T-cell, subsets, in certain situations, to achieve the necessary biological effect, antibodies to any of the aforementioned interleukins or interferons may need to be administered instead of the native molecules.

Administration of the dose can be intravenous, nasal, parenteral, oral, subcutaneous, intramuscular, topical, transdermal or any other acceptable method. The IL-4 could be administered in any number of conventional dosage forms. Parenteral preparations include sterile solutions or suspensions. Inhalation administration can be in the form of a nasal or oral spray, or by insufflation. Topical dosage forms can be creams, ointments, lotions, transdermal devices (e.g., of the conventional reservoir or matrix patch type) and the like.

The formulations and pharmaceutical compositions contemplated by the above dosage forms can be prepared with conventional pharmaceutically acceptable excipients and additives, using conventional techniques.

Presently, the IL-4 is preferably administered via the intravenous route. The solutions to be administered may be reconstituted lyopholized powders and they may additionally contain preservatives, buffers, dispersants, etc.

Preferably, IL-4 is reconstituted with 10 millimolar citrate buffer and preservative-free sterile water with the maximum concentration not to exceed 100 micrograms per milliliter and administered by continuous intravenous infusion or by intravenous injection. For continuous infusion, the daily dose can be added to 5 ml of normal saline and the solution infused by mechanical pump or by gravity.

The above references are hereby incorporated by reference for their relevant teachings of materials and methods used in the construction of the CHO expression system for hIL-4.

The present invention also involves the treatment of wounds in mammals with a therapeutically effective amount of IL-4 so as to enhance the healing of the wound. Classically, wound healing has been divided into four stages. These stages tend to occur sequentially, however, the actual physiological events can overlap. The stages are as follows starting from the time of the wound:

| STAGE | TIME |
|---|---|
| INFLAMMATORY/IMMEDIATE | 0 TO 1 HOUR |
| INFLAMMATORY/DEBRIDEMENT/EARLY | 1 TO 24 HOURS |
| REPARATIVE/INTERMEDIATE | 1 TO 7 DAYS |
| MATURATION/LATE | GREATER THAN 7 DAYS. |

The reparative phase is characterized by angiogenesis, fibroblast localization and wound contraction. Fibroblasts migrate along the fibrin lattice (i.e. scab-laid down during the first 24 hours) into the wound exudate and begin to aggregate between the neovascular structures. These fibroblasts begin the secretion of proteoglycan and soluble collagen as early as day 2. These materials form a matrix. The increase in wound tensile strength correlates with collagen production. Open wounds and wounds with significant loss of tissue must form a vascular bed to furnish the oxygen and nourishment that the reparative cells in the wound require. Proliferation of endothelial cells gives birth to capillary buds (angiogenesis), which extends to form a bed granulation tissue and is eventually covered by epithelial cells to close the wound. Inward migration of the wound edges (contraction) begins as a subset of fibroblasts having contractile properties arise in the wound.

We have discovered that IL-4 induces more than a twofold increase in collagen content. In the reparative phase of wound healing and repair, newly synthesized collagen is incorporated into the extracellular matrix thereby providing a strong scaffolding or support for new cell growth and proliferation and an increase in the tensile strength of the wound. We have also discovered that IL-4 provides selective enhancement and control of wound healing and repair during the reparative phase wound healing and repair. Not only does administration of IL-4 in accordance with this invention promote wound repair, but IL-4 may also minimize scar tissure formation and/or fibrosis caused by chemotaxis of toomany skin fibroblast cells toward the growth factor PDGF and reduce inflammation at the wound site by down regulating IL-1 induced proliferation and chemotaxis of skin fibro blast tissue cells toward the PDGF. The administration of IL-4 at or in the vicinity of wound sites during the reparative phase in accordance with this invention would be useful for any mammal compatible with the IL-4 whose immune response is not strong enough or fast enough to effect would healing and/or repair. Such mammals preferably human beings include any immunocompromised host whose immune responses have been lowered because of radiation chemotherapy administered to treat cancer or an organic transplant, a host with a genetic immunodeficieny, older people, bed-ridden people with impaired wound healing and repair functions, and diabetics.

The term "wound" as used herein includes but is not limited to open wound or cuts caused by surgical incision or injury, burns ulcers or bed sores. The term "enhancing the reparative phase of wound healing and repair" includes (1) controlling and/or enhancing the chemotaxis of human skin fibroblast tissue cells toward a chemoattractant such as PDGF present at a wound site during the reparative phase of wound healing and/or repair; (2) controlling and/or enhancing collagen synthesis in human skin fibroblast tissue cells which have migrated to and/or are present at a wound site during the reparative phase of wound healing and repair; (3) inhibiting or dampening, i.e. down-regulating the inflammation reaction caused by IL-1 induced migration of skin fibroblast tissue cells toward a chemoattractant such as PDGF present at a wound site during the reparative phase; and (4) enhancing, in a controlled way, the stimulation by the chemoattractants PDGF and especially EGF of the growth of human skin (but not lung) fibroblast tissue cells present at a wound site during the reparative phase of wound healing and repair.

We have discovered that human skin fibroblasts grown in the presence of IL-4 display an enhanced chemotaxis toward the chemoattractant PDGF in a modified Boyden chamber assay. This enhanced chemotaxis would provide an important signal in the recruitment of fibroblasts into a wound site before and during the reparative phase. We have discovered that IL-4 may dampen i.e., downregulate the ability of IL-1 to stimulate the migration of human skin fibroblast cells toward PDGF thereby minimizing scar formation and fibrosis. Thus, we have discovered that administration of IL-4, preferably topical administration of IL-4, at or in the vicinity of a wound site should promote healing and repair of wounds during the reparative stage thereof by: (1) stimulating skin fibroblast proliferation; (2) inducing collagen synthesis; (3) inhibiting IL-1 induced chemotaxis of human skin fibroblast cells toward PDGF and other chemoattractants; and (4) enhancing, in a controlled way, the stimulation by the chemoattractants PDGF of the growth of human skin fibroblast tissue cells present at a wound site during the reparative phase of wound healing and repair.

We have also unexpectedly discovered that IL-4 dramatically enhances the healing of infected wounds and the wounds of mammals afflicted with diabetes mellitus.

According to this invention, mammals are administered an effective amount of an IL-4 to enhance the reparative phase of wound healing and repair, to control and/or enhance chemotaxis of human skin fibroblast tissue cells toward a chemoattractant, to control and/or enhance collagen synthesis in human skin fibroblast tissue cells which have migrated or are present at the wound site and to inhibit or downregulate the inflammation reaction caused by IL-4 induced migration of skin fibroblast tissue cells toward a chemoattractant; and (4) enhancing, in a controlled way, the stimulation by the chemoattractants PDGF and EGF of the growth of human skin fibroblast tissue cells present at a wound site during the reparative phase of wound healing and repair.

Also, according to the present invention, infected wounds of mammals are administered a therapeutically effective amount of IL-4 to enhance the healing of the wound. The present invention further provides for a method for promoting the healing of wounds of individuals afflicted with diabetis mellitus comprised of treating the wound with a therapeutically amount of IL-4.

The amount of IL-4 which is applied to a wound depends upon the size of the wound. Preferably from about 0.1 to about 15 micrograms of IL-4 is applied per square centimeter of the wound. If a human is being treated preferably recombinant human IL-4 ("rhIL-4") is applied. Most preferably from about 1 to about 10 micrograms of rhIL-4 per square centimeter per day in single or divided doses at or in the vicinity of the wound site.

The amount, frequency and period of administration will vary depending upon factors such as the extent and severity of wound, age and physical condition of the patient. Usually, the administration of IL-4 will be once but it could also be daily, initially, and it may continue periodically prior to or during the reparative phase of wound healing and repair. Dosage amount and frequency may be determined during initial examination of the wound and the magnitude of the effect of IL-4 upon reparative phase of wound healing and repair.

The formulations of pharmaceutical compositions contemplated by the above dosage forms can be prepared with conventional pharmaceutically acceptable excipients and additives, using conventional techniques.

Presently, it is most preferred to administer IL-4 topically in a collagen gel such as are available from Bausch & Lomb Pharmaceuticals, Clearwater, Fla. in the form of collagen shields (See I. Finkelstein et al. *Current Eye Research*, 9 (7) 653–659 (1990). The topical dosage in the preferred collagen gel is in the range of about 100 nanograms to about 1 microgram of IL-4 per ml of gel, preferably about 150 nanograms to about 1 microgram of IL-4 per mL of gel, more preferably about 300 nanograms to about 1 microgram of IL-4 per mL of gel, which dosages may be administered at the wound site as part of a bandage or dressing or in the vicinity of the wound as a separate patch To further complement the stimulation of human fibroblast tissue cells by IL-4 during wound healing and repair it may be useful to administer IL-4 in conjunction with other cytokines including interleukins e.g. IL-1 and interferons, e.g. gamma interferon and growth factors. Typical suitable growth factors include epidermal growth factor (EGF), platelet derived growth factor (PDGF) and transforming growth factors- alpha and beta (TGF-a and TGF-b respectively)] which growth factors have been shown to stimulate skin fibroblasts resulting in increased production of collagens and possibly glycosaminoglycans (GAG). In a preferred aspect of this invention, the administration of IL-4 in association with EGF or PDGF provides enhanced controlled stimulation of human skin fibroblast tissue cells. Gamma interferon has been shown to increase expression of the intercellular adhesion molecule (ICAM-I) in fibroblasts, whereas IL-1 has been shown to stimulate production of collagens [See D. N Sauder et al., *Lymphokine Research* (1990), Vol. 9(4), 465–473. In conjunction with these growth factors, IL-4 may act to augment and/or modulate their activities. Modulation of collagen synthesis and of GAG synthesis may help to limit scar formation, which is a frequent problem in repair of skin wounds in the facial region. In addition, application of IL-4 over a specified time course may enhance the recruitment of fibroblasts and other cell types into the wound area under repair. IL-4 may also act to modulate fibroblast responsiveness to other factors either by upregulating or by downregulating expression of factor receptors, especially IL-1.

The terms "in conjunction with" or "in association with" as used herein means IL-4 may be administered prior to, simultaneous with or just after administration of other cytokines.

EXAMPLE 1

The Effect of IL-4 on Increasing the Neutrophil Count in Mammals

*E.coli* derived human IL-4 was evaluated in a one month study in Cynomolgus monkeys. IL-4 was administered intravenously once daily at doses of 2, 10, and 25 µg/kg/day. Hematological and clinical chemical evaluation of blood samples from the monkeys were conducted at selected time points prior to, during, and one month after termination of dosing. Data was derived from a Coulter S+4 hemotology analyzer [total white count] and a manual differential count. The results as shown in FIG. 1 demonstrate the increased neutrophil count found by the present invention.

The activation of neutrophils by IL-4 may be demonstrated by the following test protocols.

METHODS

A. Isolation of Cells:

Whole blood drawn from cynomolgus monkeys four weeks after the cessation of IL-4 dosing (25 µg/kg) or vehicle was subjected to gravity sedimentation through 6% dextran, followed by alternate lysis with hypotonic saline or Tris-amonium chloride to recover leukocytes.

B. Yeast Phagocytosis Assay:

The phagocytic assay was performed by adding 300 ml of human serum, 50 ml of heat-killed yeast particles ($10^8$ organisms/ml) to 12×75 mm polypropylene tubes containing approximately $5\times10^5$ of the isolated leukocyte cells. Incubation was carried out for 90 minutes in a gyrorotary water bath at 37° C. Following centrifugation, the cell suspension was stained with 0.4% trypan blue and 0.2% eosin Y in saline. Ingested yeast remains colorless and uningested yeast stains purple allowing for accurate determination of avidity (number of yeast ingested) as well as percent phagocytic cells. Mean values obtained for these parameters were multiplied to calculate a phagocytic index for each monkey. Data were analyzed by the Student's T test comparing values from IL-4 treated monkeys to that of control monkeys receiving vehicle alone. The results are shown in Table 1 below:

TABLE 1

The Phagocytic Function of Peripheral Blood Leukocytes Drawn from Monkeys Four Weeks After IL-4 Withdrawal

| Monkey # | IL-4[a] (μg/kg) | Yeast/cell[b] | Percent[c] Phagocytic | Phagocytic Index[d] |
|---|---|---|---|---|
| 1 | 0 | 3.8 ± 0.2 | 35.0 | 130.6 |
| 2 | 0 | 3.8 ± 0.2 | 50.0 | 186.5 |
| 3 | 0 | 5.3 ± 0.2 | 45.6 | 242.1 |
| 4 | 0 | 2.6 ± 0.2 | 33.8 | 87.5 |
|   | mean[e] | 3.9 ± 0.6 | 41.1 ± 4 | 161.6 ± 33.6 |
| 5 | 25 | 4.84 ± 0.2 | 82.5 | 399.3 |
| 6 | 25 | 4.8 ± 0.2 | 70.0 | 333.2 |
| 7 | 25 | 4.7 ± 0.2 | 71.4 | 336.4 |
| 8 | 25 | 3.8 ± 0.2 | 61.9 | 232.6 |
|   | mean[e] | 4.5 ± 0.3 | 71.5 ± 4[f] | 325.4 ± 34.5[g] |

[a]Cells obtained from monkeys dosed for 4 weeks with IL-4 or vehicle followed by a 4 week washout period.
[b]Mean yeast per cell = # yeast ingested/60 cells from each monkey; Mean ± SEM based on cells counted.
[c]Percent Phagocytic cells = % of cells ingesting yeast/total cells × 100.
[d]Phagocytic Index = mean yeast/cell × % phagocytic cells.
[e]Mean ± SEM of the individual values for the monkeys.
[f]P < 0.002, Student's T test, control vs. IL-4.
[g]P < 0.014, Student's T test, control vs. IL-4

C. NBT Assay:

Following isolation as above, leukocytes from cynomolgus monkeys were resuspended in 0.2 ml RPMI-1640 containing 2% heat-inactivated fetal bovine serum and distributed into 12×75 mm polypropylene test tubes. To each tube, 0.1 ml of a 2 mg/ml solution of nitroblue tetrazolium (NBT) in 2% RPMI and 0.1 ml of a 0.25 mM stock of freshly prepared phorbol 12-myristate 13-acetate (PMA) in 2% RPMI were added to the cells. The cell suspension was incubated in a 37° C. water bath for 30 minutes. After incubation, the tubes were centrifuged and supernatants were removed from the cell pellet. Cell pellets were dried for 1 hour at 37° C. before extraction with N,N-dimethylformamide (DMF). One ml of DMF was added to the cell pellet, vortexed, and immediately incubated at 85° C. for 20 minutes. The tubes were centrifuged and the colored DMF was collected for spectrophotometric analysis at 560 nm against a DMF blank. All measurements were performed within 30 minutes of post-termination of incubation.

Calculation of NBF (μg/ml) was done from a standard curve prepared by using serial dilutions of a 2 mg/ml NBT stock solution spotted on Whatman filter strips and dried. For the standard curve, NBT was reduced by exposure to 1 mM ascorbate solution in 0.2N NaOH for 20 min. at room temperature in the dark. The filters were extracted with DMF and read at 560 nm. Calculation of the NBF/cell was obtained by dividing NBF, μg/ml, by the number of cells per ml of sample. The results are shown in Table 2 below:

TABLE 2

The Phagocytic Function of Peripheral Blood Leukocytes Drawn from Monkeys Four Weeks after IL-4 Withdrawal Measured by NBT Reduction.

| Monkey # | IL-4[a] Dosage (μg/kg) | ABS (560 nm) | NBF/ml (ug/ml) | NBF[b] pg/cell |
|---|---|---|---|---|
| 1 | 0 | 0.095 | 3.9 | 0.3 |
| 2 | 0 | 0.075 | 3.1 | 0.3 |
| 3 | 0 | 0.113 | 4.5 | 0.7 |
| 4 | 0 | 0.033 | 1.5 | 0.3 |
|   |   |   | mean | 0.4 ± 0.1[c] |
| 5 | 25 | 0.213 | 8.3 | 1.1 |
| 6 | 25 | 0.316 | 12.1 | 0.7 |
| 7 | 25 | 0.483 | 18.5 | 1.0 |
| 8 | 25 | 0.163 | 6.5 | 0.7 |
|   |   |   | mean | 0.9 ± 0.1[c,d] |

[a]Cells obtained from monkeys dosed for 4 weeks with IL-4 or vehicle followed by a 4 week washout period.
[b]NBF, pg per cell, calculated from NBF μg/ml/total cells in the sample. Cell number obtained by hemocytometer count using Turks solution prior to assay.
[c]mean ± SEM of the individual values for the monkeys.
[d]P < 0.02, Student's T Test, control vs. IL-4.

The above results demonstrate that phagocytic index of leukocytes obtained from IL-4 treated monkeys four weeks post-dosing was increased significantly over leukocytes obtained from control animals. This elevation in the phagocytic index was due to the increase in the percentage of cells ingesting yeast. There was a slight increase in the avidity of the cells (number of yeast infested per cell) from the IL-4 post-dosage group. The NBT dye reduction response measured as pg/cell of NBF was increased in cells taken form IL-4 treated monkeys as compared to cells from monkeys in the vehicle-control group.

These two assays, yeast cell ingestion and NBT dye reduction, are measures of phagocytosis and the metabolic changes (hexose monophosphate shunt activity) that are important stages in the sequence of events that lead to the destruction of infectious agents. The increases obtained in both parameters indicate that IL-4 can increase or amplify the phagocytic response.

EXAMPLE 3

Induction of Differentiation of Leukemic Cell Lines

U937 is a cell line (ATCC CRL 1593) established from malignant cells from a patient with diffuse histiocytic leukemia (Sunstrom, C. and Nilsson K. *Int. J. Cancer,* 17:565–577, 1976). This cell line exhibits characteristics that indicate it is an immature monocyte.

HL-60 is a cell line (ATCC CCL 240) established from a patient with acute promyelocytic leukemia. These cells exhibit characteristics that indicate it is an immature neutrophil.

IL-4 is able to induce differentiation of these 2 immature cells as defined by an increase in phagocytic function, an increase in activation of the hexose monophosphate shunt (NBT reduction) which is a metabolic necessity for phagocytosis, an increase in the percentage of cells able to take up a stain specific for mature neutrophils (napthol chloroacetate esterase) or mature monocytes (alpha napthyl acetate esterase) and an increase in cells positive for surface markers as demonstrated by FACS analysis for mature monocytes or mature neutrophils.

The effect of IL-4 on maturation of myeloid cells may be demonstrated by the following test procedures:

NBT (NITROBLUE TETRAZOLIUM) REDUCTION TO FORMAZAN

Cellular Measurement of Hexose Monophosphate Shunt Activation Associated with Respiratory Burst.

Muller, et al., *Agents & Actions*, 11:384 (1981).

Baehner, et al., *NEJM*, 278:971 (1968).

Salin and McCord, *J. Clin. Invest.*, 54:1005 (1974).

Standardized for use with U-937 and HL-60 cell lines

1. Harvest target cells sufficient for $1 \times 10^6$ cells/well assay. Spin down in a Sorvall at 1200 rpm 5 min. Wash with PBS and respin.
2. Bring up cells in sufficient RPMI+2% FBS (2%) to aliquot 0.2 ml/well assay.
3. Aliquot cells at 0.2 ml/well in 24-well flat-bottom plate.
4. Add 0.1 ml of 20 uM PMA in 2% (to each well).
5. Add 0.1 ml of 2 mg/ml NBT in 2% (to each well).
6. Incubate plate at 37° C. for 30 min.
7. Immediately remove 0.1 ml of cells and spin down at 200 rpm (low acceleration) for 5 min. using Shandon Cytospin.
8. Counterstain with Diff-Quick system and mount with coverslip for counting.

The yeast phagocytosis assay as described above was also performed for both cell lines using the same methodology.

NAPTHOL AS-D CHLOROACETATE ESTERASE STAIN FOR PMNS

Yam, et al., *Am. J. Clin. Path.*, 55:283 (1971).

Li, et al., *J. Histiochem. Cytochem.*, 21:1 (1973).

Standardized for staining HL-60 cell line.

1. Spin down $1 \times 10^5$ and $5 \times 10^5$ cells onto microscope slide at 200 rpm (low acceleration) 5 min. using Shandon Cytospin.
2. Fix slide for 2 min. in Citrate-Acetone-MeOH fixative at room temperature.
3. Wash in deionized water and air-dry 20 min.
4. Stain slides in AS-D stain for 30 min. at 37° C. in dark.
5. Wash 3× in deionized water.
6. Counterstain in acid-hematoxylin stain 5 min.
7. Wash 3× in deionized water, air-dry, mount with coverslip.

Citrate-Acetone-MeOH Fixative:

Dilute Citrate concentrate 1:9 with deionized water.

Add 18 ml Citrate solution, 27 ml Acetone, and 5 ml absolute methanol.

Store at room temperature.

Prepare daily.

AS-D Stain:

Dilute Trizmal 6.3 1:9 with deionized water.

Warm 50 ml dilute Trizmal 6.3 to 37° C. and add with constant stirring contents of 1 capsule of Fast Corinth V salt. When salt is completely dissolved add 2 ml of Napthol AS-D Chloroacetate solution. The solution will appear quite turbid. Continue stirring 15–30 min. and add to coplin jar. Do not filter.

AS-D Solution:

Dissolve 1 capsule of Napthol AS-D Chloroacetate (20 mg) in 2 ml of dimethyl formamide. Prepare immediately before use.

Use Sigma kit 90—Naphthol AS-D Chloroacetate.

alpha NAPTHYL ACETATE ESTERASE STAIN FOR MACROPHAGES

Yam, et al., *Am. J. Clin. Path.*, 55:283 (1971).

Li, et al., *J. Histiochem. Cytochem.*, 21:1 (1973).

Standardized for staining U-937 cell line.

1. Spin down $1 \times 10^5$ and $5 \times 10^5$ cells onto microscope slide at 200 rpm (low acceleration) 5 min. using Shandon Cytospin.
2. Fix slide in Citrate-Acetone-MeOH Fixative 30 min. at room temperature.
3. Wash in distilled/deionized water and air-dry 20 min.
4. Stain slides in NE stain at 37° C. for 30 min. in dark.
5. Wash 3× in distilled/deionized water.
6. Counterstain in Mayer's Hematoxylin 5 min. at room temperature
7. Wash in distilled/deionized water, air-dry, mount with coverslip.

Citrate-Acetone-MeOH Fixative:

Dilute Citrate concentrate 1:9 with distilled/deionized water.

Add 18 ml Citrate solution, 27 ml Acetone, and 5 ml absolute methanol.

Store at room temperature.

Prepare daily.

NE Stain:

Dilute Trizmal 7.6 1:9 in distilled/deionized water.

Warm dilute Trizmal 7.6 to 37° C. and add with constant stirring contents of 1 capsule Fast Blue RR salt. When salt is completely dissolved add 2 ml of NE solution. The solution will be yellow and slightly turbid. Continue stirring for 15–20 min. and add to coplin jar. Do not filter.

NE Solution:

Dissolve 1 capsule (20 mg) of alpha napthyl acetate to 2 ml of ethylene glycol monomethyl ether. Prepare immediately before use.

Use Sigma kit 90—alpha napthyl acetate.

The results from the above procedures using HL-60 cells and U-937 cells are set forth below in Tables 3 and 4.

TABLE 3

The Effect of *E. coli*-derived IL-4 on the Function and Differentiation of HL-60 Cells.

| Treatment[a] | Yeast/Cell[b] | % Phagocytic Cells[c] | Phagocytic Index[d] | NBT[e] | CAE[f] |
|---|---|---|---|---|---|
| Media | 2.4 ± 0.3 | 18 ± 5 | 42 ± 12 | 17 ± 2 | 21 ± 5 |
| IL-4 | | | | | |
| 250 U/ml | 5.5 ± 1.4[g] | 42 ± 5[g] | 225 ± 45[g] | 33 ± 3 | 62 ± 3[g] |
| 25 U/ml | 5.1 ± 1.1[h] | 41 ± 4[g] | 207 ± 37[g] | 39 ± 4[g] | 56 ± 6[g] |
| 2.5 U/ml | 5.4 ± 1.5[g] | 36 ± 3[g] | 184 ± 38[g] | 35 ± 4[g] | 53 ± 3[g] |
| 0.25 U/ml | 3.7 ± 1.0 | 27 ± 5 | 96 ± 24[h] | 36 ± 4[g] | 40 ± 2[g] |
| 0.025 U/ml | 3.1 ± 0.6 | 25 ± .6 | 75 ± 18 | 23 ± 2 | 32 ± 7 |
| DMSO | 3.6 ± 0.4[g] | 71 ± 10[g] | 259 ± 54[g] | 92 ± 2[g] | 56 ± 2[g] |

[a]HL-60 cells incubated for 6 days in media containing the designated contrations of IL-4 or DMSO. Cultures fed with IL-4 or DMSO on day 3.

TABLE 3-continued

The Effect of E. coli-derived IL-4 on the Function and Differentiation of HL-60 Cells.

| Treatment[a] | Yeast/Cell[b] | % Phagocytic Cells[c] | Phagocytic Index[d] | NBT[e] | CAE[f] |
|---|---|---|---|---|---|

[b]Mean ± SEM of 4 separate experiments; Mean yeast/cell = # yeast ingested/30 cells.
[c]Percent Phagocytic Cells = Number of cells ingesting yeast/total cells × 100 Mean ± SEM of 4 separate experiments.
[d]Phagocytic index – Mean yeast/cell × % Phagocytic cells.
[e]Percent of Cells positive for formazan; Mean ± SEM of 4 separate experiments.
[f]Percent of Cells positive for Chloroacetate esterase; Mean ± SEM of 4 separate experiments.
[g]$P \leq 0.05$; Student's T test.
[h]$P \leq 0.10$; Student's T test.

TABLE 4

The Effect of a E. coli derived IL-4 on the Function and Differentiation of U937 cells.

| Treatment[a] | Yeast/Cell[b] | % Phagocytic Cell[c] | Phagocytic Index[d] | NBT[e] | aNE[f] |
|---|---|---|---|---|---|
| Media | 1.3 ± 0.4 | 10 ± 2 | 15 ± 3 | 5 ± .5 | 16 ± 4 |
| IL-4 | | | | | |
| 250 U/ml | 2.5 ± 2[g] | 25 ± 5[g] | 57 ± 15[g] | 38 ± 7[g] | 66 ± 7[g] |
| 25 U/ml | 2.4 ± .2[g] | 25 ± 5[g] | 63 ± 17[g] | 41 ± 1[g] | 64 ± 6[g] |
| 2.5 U/ml | 2.5 ± .2[g] | 20 ± 3[g] | 51 ± 10[g] | 33 ± 2[g] | 54 ± 7[g] |
| .25 U/ml | 1.9 ± .3[g] | 21 ± 5[h] | 43 ± 14[h] | 28 | 44 ± 4[g] |
| .025 U/ml | 1.7 ± .1[g] | 16 ± 4 | 28 ± 8 | 27 ± 2[g] | 29 ± 3 |

[a]U937 cells incubated for 6 days in media containing the designated concentrations of IL-4. Cultures fed on May 3.
[b]Mean yeast/cell = # of yeast ingested/30 cells; Mean ± SEM of 4 experiments.
[c]Percent of Phagocytic cells = # of cells ingesting yeast/total cells × 100; Mean ± SEM of 4 experiments.
[d]Phagocytic Index = Mean yeast/cell × % Phagocytic cells; Mean ± SEM of 4 experiments.
[e]Percent of cells positive for NBT/cells Mean ± SEM of 4 experiments.
[f]Percent of cells positive for alpha-Napthyl esterase; Mean ± SEM of 4 experiments.
[g]$P \leq 0.05$; Student's T test.
[h]$P \leq 0.10$; Student's T test.

FACS Analysis of Monocyte and Neutrophil Surface Markers:

HL-60 and U-937 cells were incubated in T-75 flasks at 37° C. and 5% $CO_2$ with increasing levels of IL-4 (E. coli-derived rhu IL-4: 8-ILE-1002) or controls; cells were split and fed on day 3. On days 1, 3, and 6 cells were removed, washed with RPMI 1640 and blocked with human heat-aggregated IgG to reduce potential Fc interference. After washing again with RPMI 1640, cells resuspended in 50 μl of diluted antibody (see following table for the monoclonal antibody panel) and incubated 30 minutes on ice. The cells were then washed in PBS, resuspended in 100 μl of diluted FITC-conjugated goat-anti-mouse IgG or $IgG_{2b}$ and incubated for 30 minutes on ice. After the incubation of the second antibody, the cells were washed repeatedly in PBS, then resuspended in 1 ml PBS and run on a Becton-Dickinson FACScan for cytofluorometric analysis. Isotype controls for murine $IgG_{2b}$ and $IgG_1$ and second antibody controls were run for increase in positive cells above a constitutive expression level (i.e., IL-4 induction of enhanced expression).

Monoclonal Antibody Panel:

| Mab | Ig Isotype | Cluster of Differentiation | Specificity |
|---|---|---|---|
| WEMG11 | $mulgG_1$ | UNK. | gp 110: Granulocytes |
| FMC 32 | $mulgG_1$ | UNK. | Myelomonocytes |
| OKM-1 | $mulgG_{2b}$ | CD11b | CR-3 |
| anti-Leu M5 | $mulgG_2b$ | CD11c | a chain (gp 150-95) |
| Anti-CR-1 | $mulgG_1$ | CD35 | C3b, CR-1 |
| anti-Leu M3 | $mulgG_{2b}$ | CD14 | Monocytes |

The results from the FACS Analysis above are shown in FIGS. 5 and 6.

EXAMPLE 4

Use of IL-4 to Enhance Wound Healing at the Reparative Phase

METHODS

Human Skin Fibroblast Cell Lines

Human skin fibroblast cell lines obtained from the American Type Culture Collection (ATCC) (CCD 27sk ATCC #CRL-1475, CCD 19sk ATCC #CRL-1471, and CCD 34 lu ATCC #CRL 1491) were maintained in Dulbecco Modified Eagles Medium (DMEM) or Modified Eagles Medium (MEM) which were supplemented with 10% fetal bovine serum, as recommended by the ATCC. Typically, the fibroblast cell line cultures were used up to passage 20 where one passage was equivalent to 2-3 cell doublings. CCD 27sk are normal (control) human fetal fibroblasts derived by skin biopsy from apparently normal individuals.

Lymphokines and Growth Factors

CHO-derived recombinant human interleukin-4 (rhIL-4) /was obtained from Schering-Plough Union, N.J. (specific activity 5×10$^7$ u/mg). Human platelet-derived growth factor (PDGF) (BB homodimer) was purchased from Genzyme Corporation Boston. Mass. Epidermal growth factor (EGF) and PDGF were purchased from Collaborative Research, New Bedford, Mass.

Antibodies

Monoclonal antibodies against recombinant human IL-4 (25D2) were prepared at Schering-Plough Research, Bloomfield, N.J. by established procedures and are also available from Genzyne Corporation. Anti-IL-5 (TRFK) monoclonal antibodies were supplied by Schering-Plough Research, Bloomfield.

According to this invention human fibroblast cells are grown in the presence of IL-4. Depending upon the format of the experiment, one or more of the following are measured: (1) DNA synthesis; (2) collagen synthesis; (3) chemotaxis toward PDGF and other chemoattractants; (4) inhibition of IL-1 stimulated chemotaxis; and (5) enhanced PDGF/ EGF—stimulation of human skin fibroblast tissue cells.

Measurement of ($^3$H)-thymidine incorporation associated with DNA synthesis in human skin fibroblast cells was performed using methods of Monroe et al., *Clinical Immunology and Immunopathology*, 49:292-298 (1988); and Thornton, S. C., et al., *J. Leukocyte Biology* 47:312-320 (1990). (CCD 27sk)

20,000 human fibroblasts (CCD 27sk) were seeded into 24-well culture dishes. Following overnight incubation at 37° C., non-adherent cells were removed and the cell layers washed twice with serum-free medium. Cell cultures were then maintained in medium containing 0.1%, 1%, or 2% fetal calf serum (FCS) for 48 hours. Human recombinant interleukin-4, rhIL-4, (0.1-100 units/well) was then added and the incubation continued for an additional 72 hours. 1 µCi ($^3$H)-thymidine obtained from New England Nuclear was added per well overnight. Incorporation of ($^3$H)-thymidine was determined by established procedures of Monroe.

In some instances fibroblast cultures were not starved in medium with 1-2% FCS, but throughout the control experiment the assay medium contained 10% FCS and rhIL-4.

The results of this experiment are graphically displayed in FIG. 4 wherein the ability of IL-4 to stimulate DNA synthesis in human skin fibroblasts was measured by incorporation of ($^3$H)-thymidine. The induction of DNA synthesis by IL-4 is dependent upon the concentration of fetal calf serum in the assay medium. Such a dose-dependent result is common for other classical growth factors such as EGF and TGF-β. Thus, we would expect that hIL-4 would stimulate DNA synthesis in human skin fibroblast cells in a clinical model.

Another cell proliferative experiment in accordance with procedure exactly analogous to the above described procedures were followed except that monoclonal antibodies against rhIL-4 (25D2) were added. No DNA synthesis was observed. In another cell proliferation experiment the above described procedures were followed except that the anti IL-5 (TRFK) monoclonal antibodies were added but no dampening of DNA synthesis by IL-4 was observed

EXAMPLE 5

IL-4 Induced Synthesis of Collagen in Human Skin Fibroblasts

Measurement of collagen synthesis was run in accordance with the procedures of Monroe et al., *Clinical Immunology and Immunopathology*, 49, 229-298 (1988), and CCD 27sk human skin fibroblasts were seeded into 24-well Primaria plates and incubated with 0.1 to 500 units/mL of CHO-dedved IL-4 as described for Example 1. Cell monolayers were pulsed 6 hours with 10 µCi ($^3$H)-proline (New England Nuclear Corp). Plates were placed on ice and the cells scraped into 200 mL of 0.2N NaOH and transferred to polypropylene tubes. Two mL of 50% trichloroacetic acid (TCA)/5% tannic acid was added and the incubation continued for 1 hour on ice. The tubes were centrifuged at 4000 g for 30 minutes at 4° C., and the pellets were washed 3 times with the same TCA/tannic acid solution used previously and then 3 times with acetone. Pellets were resuspended in 0.5N NaOH/0.5N acetic acid buffer. Aliquots were incubated with this buffer with or without collagenase, which was obtained from Boehringer Mannheim Biochemicals Indianapolis, Ind., for 90 minutes at 4° C. 500 mL of TCA/tannic acid and 100 mL 1 mg/mL bovine serum albumin (BSA) were added and the tubes incubated for 30 minutes at 4° C. Tubes were then centrifuged at 4000 g for 30 minutes. Supernatants were counted with a scintillation counter. Percent collagen synthesis was determined as follows:

$$\% \text{ collagen synthesis} = \frac{\text{collagenase released} - \text{background}}{\text{collagenase resistant} \times 5.4 \times \text{collagenase released}} \times 100.$$

The data of this experiment graphically shown in FIG. 5 demonstrate that incubation of human skin fibroblasts (CCD 27sk) with IL-4 CHO-derived results in more than a two-fold increase in type I and/or type III collagen synthesis.

EXAMPLE 6

IL-4 Induced Chemotaxis of Human Skin Fibroblasts

The procedures of Adelman-Grill, B. C., and Cully, Z. J., *Cell Physiology* 143:172-177 (1990) and of Senior, R. M., et al., *J. Clin. Invest.* 70:614-618 (1982) were used in the following chemotaxis experiment with the following modifications.

A. The ability of rhIL-4 to affect the migration of CCD 25sk human skin fibroblast cells was measured using a modified Boyden chemotaxis chamber assay. A filter consisting of a polycarbonate membrane with 8 µm pores (Nucleopore Corp., Pleasanton, Calif.) separated each well into upper and lower compartments. The filters were coated by soaking in a solution of Vitrogen (Collagen Corporation, Palo Alto, Calif.) for 4 hours at room temperature, washed with distilled water, and then air-dried. The lower compartment was filled with 240 ml of PDGF containing control medium, covered with the membrane and 350 ml of cell suspension (1.5-3×10$^5$) added to the top. The suspensions of fibroblasts were prepared by trypsinization of confluent monolayers which had been incubated with varying concentrations of rhuIL-4 (0.1-100 u/mL) for 3 days prior to assay. The assembled modified Boyden chemotaxis apparatus was placed in a humidified incubator at 37° C. for 4 hours, after which the membrane was removed, fixed with 95% ethanol, inverted, and stained with hemotoxylin. Cell migration was determined under a high power microscope (×400) by counting cell nuclei on the lower membrane. Normally, 3-4 fields were counted per membrane. Cell migration was expressed as the mean of cells per field of a triplicate determination.

B. Effect of IL-4 on chemotaxis of human skin fibroblast cells toward PDGF and zymosan was determined using the procedure of Experiment 3A in the presence 4 mg of PDGF and zymosan.

In the experiment depicted in FIG. 6, human skin fibroblasts cells (CCD 27sk) grown in the presence of rhIL-4 were tested for their ability to migrate toward platelet-derived growth factor (PDGF; 4 nanograms). The results show a concentration-dependent increase in migration toward PDGF that is induced by IL-4. In contrast, chemotaxis toward zymosan-activated human serum decreases. We expect that this new activity for IL-4 to modulate chemotaxis toward different chemoattractants should be useful in clinical therapy in healing and repairing wounds in the reparative phase.

EXAMPLE 7

Effect of IL-4 on Chemotaxis of IL-1 Treated Human Fibroblasts

Effect of IL-4 on chemotaxis of IL-1-treated CCD 27sk human skin fibroblast cells toward PDGF was run in accordance with the procedures of Example 6 with the following modifications.

Human skin fibroblasts (CCD 27sk) were pretreated with rhIL-1 (Genzyme) (10 or 100 units/mL) for 24 hours and then grown in the absence and in the presence of rhIL-4. Ratios of IL-1 units to IL-4 units were varied over the following range: 1/0; 1/10; 1/100; 10/0; 10/10 and 10/100. Cells treated in this manner were then tested for their ability to migrate toward platelet-derived growth factor (PDGF; 4 ng). The results graphically depicted in FIG. 7 demonstrate a concentration-dependent decrease in migration toward PDGF caused by IL-4. As indicated by the results shown in FIG. 4, this new activity for IL-4 in modulation of IL-1 induced chemotaxis could be useful in clinical therapies for the reparative phase wound healing and repair as well as in treating inflammation induced by IL-1.

EXAMPLE 8

Enhancement of Stimulation by IL-4 of PDGF Treated Fibroblasts

The potential of rhIL-4 to enhance the stimulation by PDGF of the growth of human skin fibroblast tissue cells was determined in accordance with the procedure of R. Margis et al. *Analytical Biochemistry* (1989), Vol 181, 209–211.

Figure 8A:
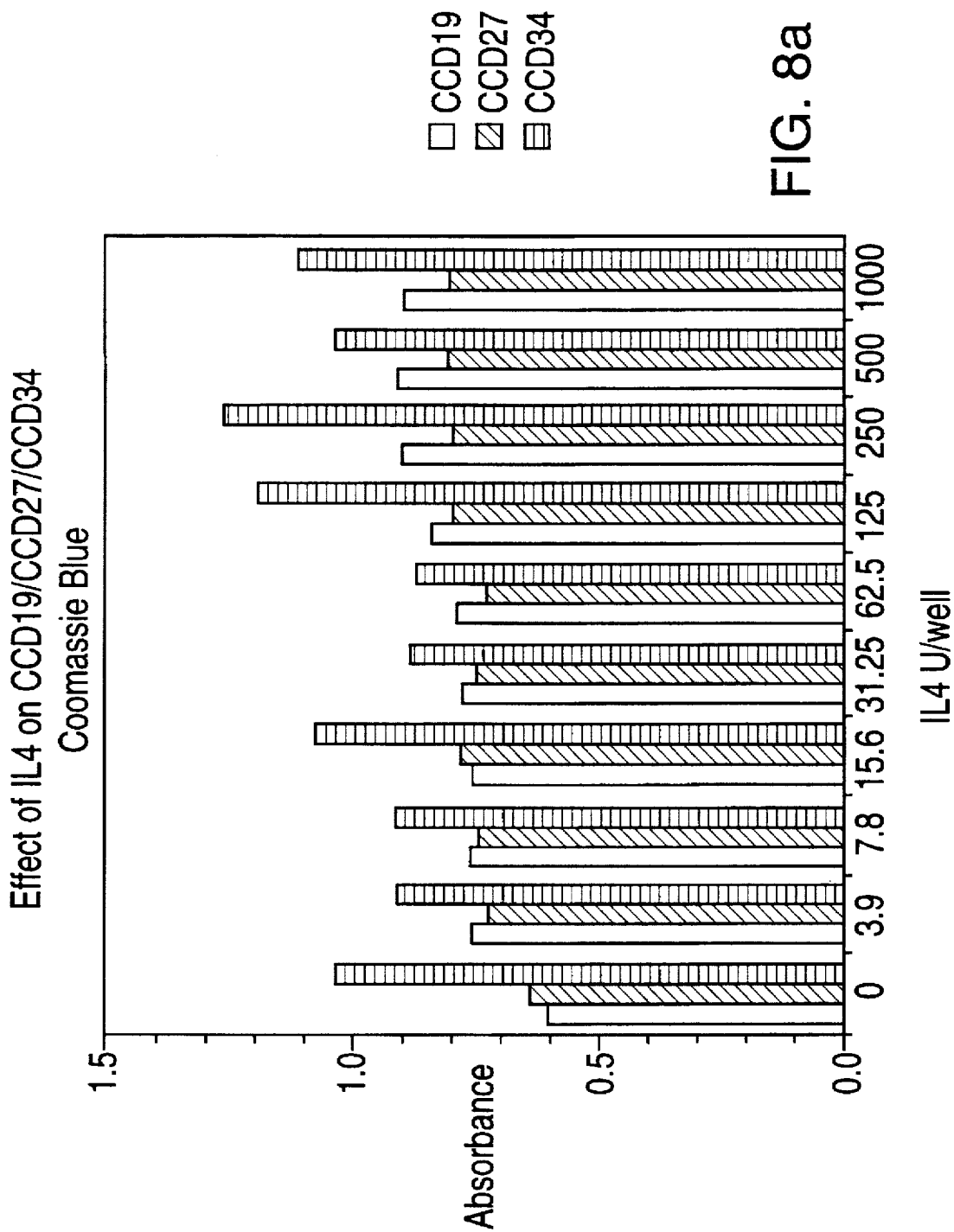
FIG. 8a is a graphic representation of the effect of IL-4 on growth of human skin fibroblast tissue cells CCD 19sk, CCD 27sk and human lung tissue cells CCD 34 lu.

A. Human skin fibroblast cells, CCD 19sk, CCD 27sk and CCD 34 lu (3,000 to 5,000 per well) were plated in 96-well plates (Primaria-Falcon). Two fold serial dilutions of rhIL-4 (1000, 500, 250, 125, 62.5, 31.25, 15.6, 7.8, 3.9) were added in DMEM supplemented with 10% FCS. After 72 hours of culture, spent medium was removed and cell number determined using the following spectrophotometric assay. After the medium was removed, the cell layer was washed with phosphate buffered saline (PBS) (pH 7.2). The cells were fixed with 40% formalin in PBS. Cells were stained according to the procedure of Margis et al., with a solution of 0.2% coomassie (BioRad) in 10% acetic acid and 40% methanol (50 ml per well). After 60 min, the stain was removed. The wells were then washed with distilled water and the dye was eluted by adding 0.1N NaOH in 50% methanol (50 ml). The absorbance of each well was read at 595 nm on a Titertek Multiscan MC, available from Dynatech Labs, Chantilly, Va. The validity of this assay for determining cell number was previously assessed by comparing absorbance at 595 nm with known cell numbers measured by hemocytometer counting. The results of the effect of IL-4 on stimulation of human fibroblast is graphically presented in FIG. 8a.

B. The effect of PDGF on the growth of the human skin and lung fibroblast tissue cells was determined in accordance with the procedure of Example 8a except that PDGF was added to each well by two fold serial dilution: (2, 1, 0.5, 0.25, 0.125, 0.0625, 0.0313, 0.0156, 0.0078 nanograms/well). The dose-dependent stimulation of human skin tissue cells by PDGF is graphically shown in FIG. 8b.

C. The dose-dependent enhancement by IL-4 on the stimulation of human skin but not lung tissue cells was determined in accordance with the procedure of Example 8A except that IL-4 and PDGF were added into each well.

The dose-dependent enhancement by IL-4 of the stimulation by PDGF of the growth of human skin fibroblast tissue cell lines is graphically shown in FIG. 8c.

EXAMPLE 9

Dose-dependent Enhancement by IL-4 of Human Skin Fibroblasts

The dose-dependent enhancement by rhIL-4 of the stimulation of human skin fibroblast tissue cell was determined in accordance with the procedures of Example 8A except that EGF was used in place of PDGF.

Figure 9A:
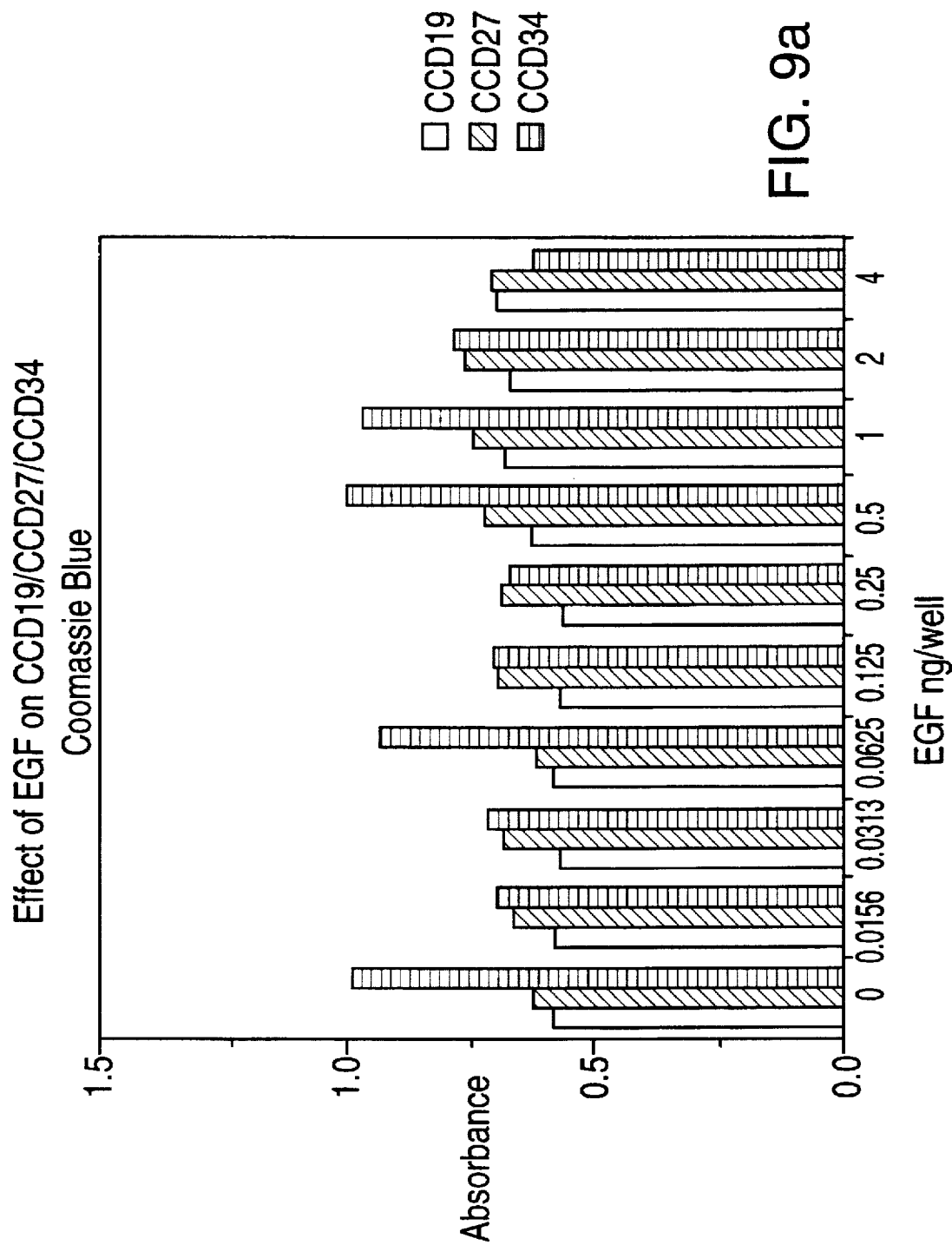
FIG. 9a is graphic representation of the effect of EGF on the growth of human skin fibroblast and lung tissue cells.

The dose-dependent effect of EGF on growth of human fibroblast skin tissue cells is shown in FIG. 9a and the rhIL-4 dose-dependent enhancement of the stimulation by EGF of human skin (but not lung) fibroblast tissue cell growth is shown in FIG. 9b. The results of FIG. 9b predict that the administration of IL-4 at or in the vicinity of the wound site would accelerate wound healing and repair by enhancing the stimulation of human skin fibroblast cells by EGF already present at or being released at or in the vicinity of the wound site. No stimulation in the growth of human lung tissue cells was observed. Results of these experiments have been confirmed by direct cell count via hemocytometer.

EXAMPLE 10

In vivo Acceleration of Wound Healing Using IL-4

Seventy-two Sprague-Dawley male rats weighing 250–300 grams were anesthetized with intraperitoneal pentobarbital 35 mg/kg. A copper template designed with four 1.5 cm$^2$ holes was fitted to the curvature of each rat's back. Using this template, four full thickness defects including the panniculus carnosus were created in the midline of each rat.

The rats were divided into eight groups. The wounds of the first five groups were not infected while the wounds of the last four groups were intentionally contaminated with $5 \times 10^5$ *E. coli.*

Control Group 1 contained 10 rats. The wound of each rat was injected with 0.1 ml of saline vehicle once a day for five days.

Group 2 contained 10 rats. The wound of each rat was injected with 0.1 mg of murine IL-4 per square centimeter area of the wound once a day for five days.

Group 3 contained 10 rats. The wound of each rat was injected with 1.0 mg of murine IL-4 per square centimeter area of the wound once a day for five days.

Group 4 contained 9 rats. The wound of each rat was injected with 10.0 mg of murine IL-4 per square centimeter area of wound once a day for five days.

Group 5 Infected Control Group contained 9 rats. The wound of each rat was contaminated with $5\times10^5$ E. coli and 0.1 ml of saline vehicle was injected into the wound each day for five days.

Group 6 contained 8 rats having infected wounds. The wound of each rat was contaminated with $5\times10^5$ E. coli. The wound of each rat was injected with 0.1 mg of murine IL-4 per square centimeter area of wound once a day for five days.

Group 7 contained 7 rats having infected wounds. The wound of each rat was contaminated with $5\times10^5$ E. coli. The wound of each rat was injected with 1.0 mg of murine IL-4 per square centimeter area of wound once a day for five days.

Group 8 contained 9 rats having infected wounds. The wound of each rat was contaminated with $5\times10^5$ E. coli. The wound of each rat was injected with 10.0 mg of murine IL-4 per square centimeter area of wound once a day for five days.

The "contaminated" wounds were inoculated with $5\times10^5$ E. coli ATCC #25922 obtained from fresh 18-hour broth culture. This produced an acutely contaminated wound. After surgery, the rats were returned to their cages and given food and water libitum.

Figure 10:
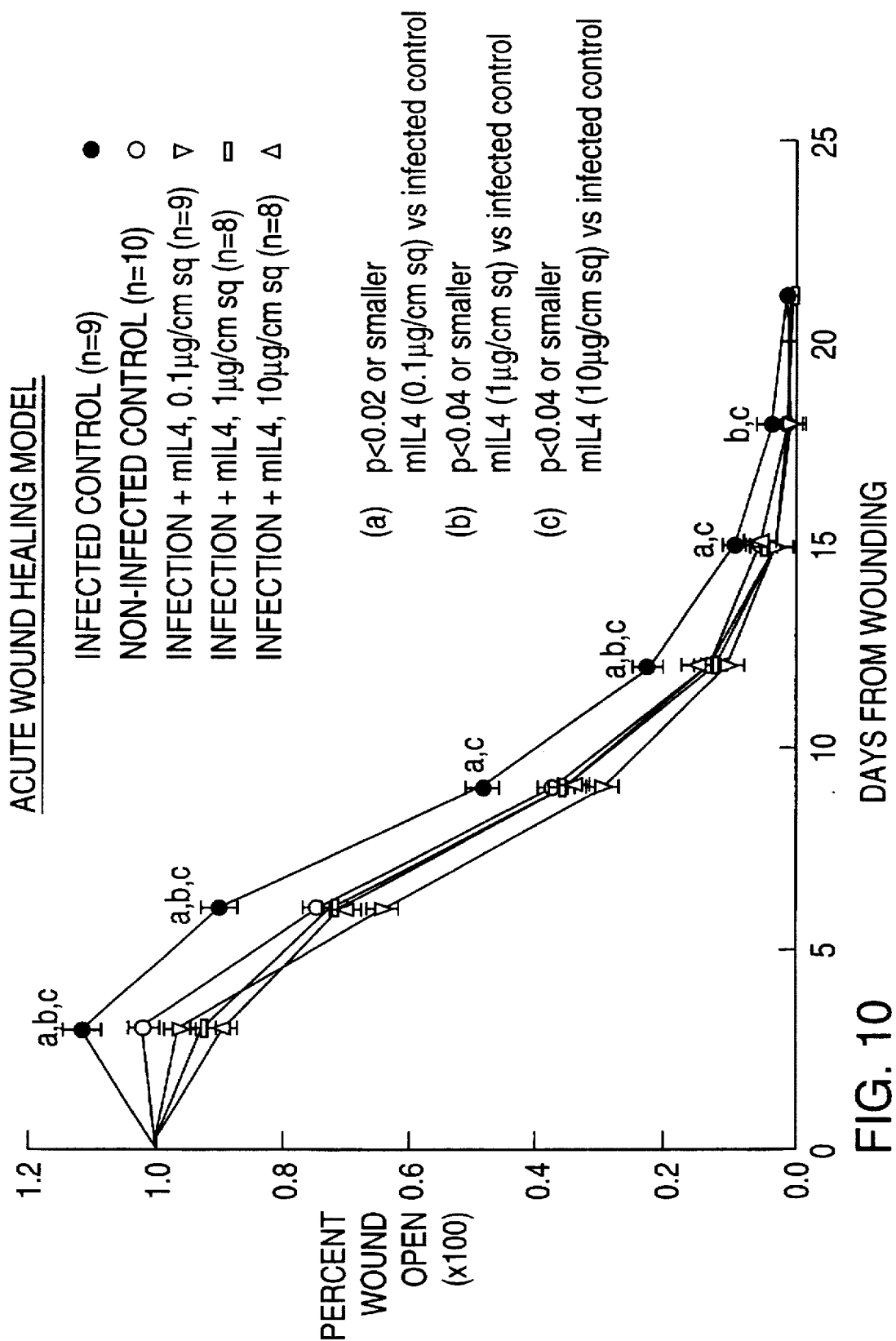
FIG. 10 is a graphic representation of the effect of IL-4 on accelerating wound closure in an acute wound healing model showing infected and non-infected wounds.

The IL-4 or vehicle was injected at the wound's edge. At the time of complete wound closure the rats were sacrificed with intraperitoneal pentobarbital overdosage. A section of the resulting scar from each of the wounds of each rat was excised as part of an 8 mm strip of dorsal tissue including panniculus carnosus. The strips were taken perpendicular to the scar. These strips, with the scar at their center were then disrupted using an INSTRON® tensiometer with a 5 kg tension load cell and a cross head speed of 10 mm per minute. The resulting breaking strengths of the wound is defined as the peak load required to rupture the scar expressed in kilograms. The results are shown in FIG. 10 and Tables 5 & 6 below.

TABLE 5

| | Non-Infected Group | | |
|---|---|---|---|
| number of rats | TREATMENT | Average Tensile Strength (kg) | STANDARD ERROR |
| 10 | CONTROL | 1.109 | ±0.044 |
| 10 | IL-4 (0.1 mg/cm²) | 0.903* | ±0.044 |
| 10 | IL-4 (1.0 mg/cm²) | 0.944* | ±0.069 |
| 9 | IL-4 (10.0 mg/cm²) | 0.981* | ±0.023 |

*p < 0.05 compared to control.

TABLE 6

| | E. coli INFECTED GROUP | | |
|---|---|---|---|
| number of rats | TREATMENT | Average Tensile Strength(kg) | STANDARD ERROR |
| 9 | INFECTION (INF) CONTROL | 0.931 | ±0.043 |
| 8 | INF + I-4 (0.1 mg/cm²) | 0.955 | ±0.044 |
| 7 | INF + IL-4 (1.0 mg/cm²) | 1.111* | ±0.063 |
| 9 | INF + IL-4 (10.0 mg/cm²) | 0.994 | ±0.051 |

*p < 0.005 compared to infected control.

FIG. 10 demonstrates the effectiveness of IL-4 treatment in accelerating wound closure in an infected acute wound healing model. At all time points IL-4 was able to decrease the percent of the wound remaining open compared to the infected control. In fact, IL-4 treatment allowed healing of an infected wound at the rate normally seen for an uncompromised non-infected wound. The data in Table 6 shows that IL-4 increases the breaking strength of infected full thickness excisional wound healing.

EXAMPLE 11

Effect of IL-4 on the Wounds of Diabetic Rats

The object of the present experiment is to present an in vivo study of the ability of IL-4 to induce wound healing in diabetic rats.

Diabetes mellitus was induced in 32 rats by injecting 45 mg/kg of streptozotoxin intramuscularly. The rats were housed in individual metabolic cages and their urines were tested daily by a standard dip-stick technique to determine glycosuria and ketonuria. After three subsequent days of established diabetes, the animals were anesthetized using nembutal general anesthesia. A 6 cm wound was made on the dorsum of each rat through the full thickness of the skin and panniculus carnous using aseptic technique as described above in Experiment 10. The rats were then divided into four groups, namely, a group into which 0.1 mg of IL-4 was injected into the wound edges, a group into which 1.0 mg of IL-4 was injected into the wound edges, a group into which 10.0 mg of IL-4 was injected into the wound edges and a control group into which a saline carrier was injected into the wound edges. The IL-4 was injected to prevent loss when the animal awakens from anesthesia and begins to shiver. The wounds were then closed with two simple sutures of 5-0 nylon. The animals were allowed to recover from ther anesthesia and were returned to their cages. One half of the rats were sacrificed at seven days and the other half at fourteen days after wounding to evaluate the early and later extent of collagen maturation by means of the breaking strength of the wounds.

To determine the breaking strength of each wound one square centimeter strips of skin and subcutaneous tissue were taken perpendicular to the wound. Breaking strength was determined through the use of the INSTRON® Tensiometer 4205 with a 5 kg load and a cross-head speed of 10 mm/minute. The gain in breaking strength has been shown to correlate well with the deposition and maturation of collagen in the wound. The results are shown in FIGS. 11 & 12.

Figure 11:
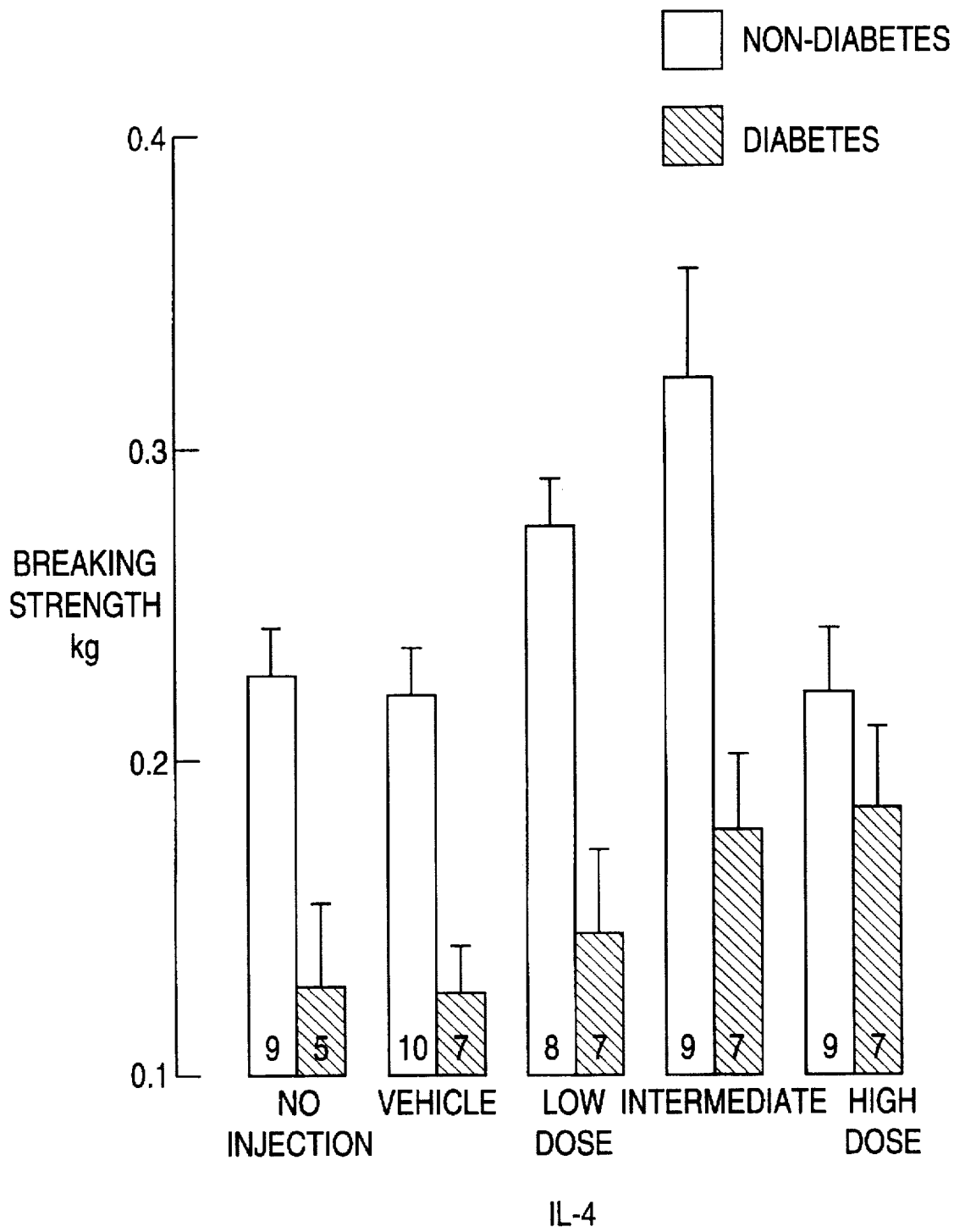
FIG. 11 is a graphic representation demonstrating the effectiveness of IL-4 in increasing the breaking strength of wounds in non-diabetic and diabetic animals at 7 days after wounding.
Figure 12:
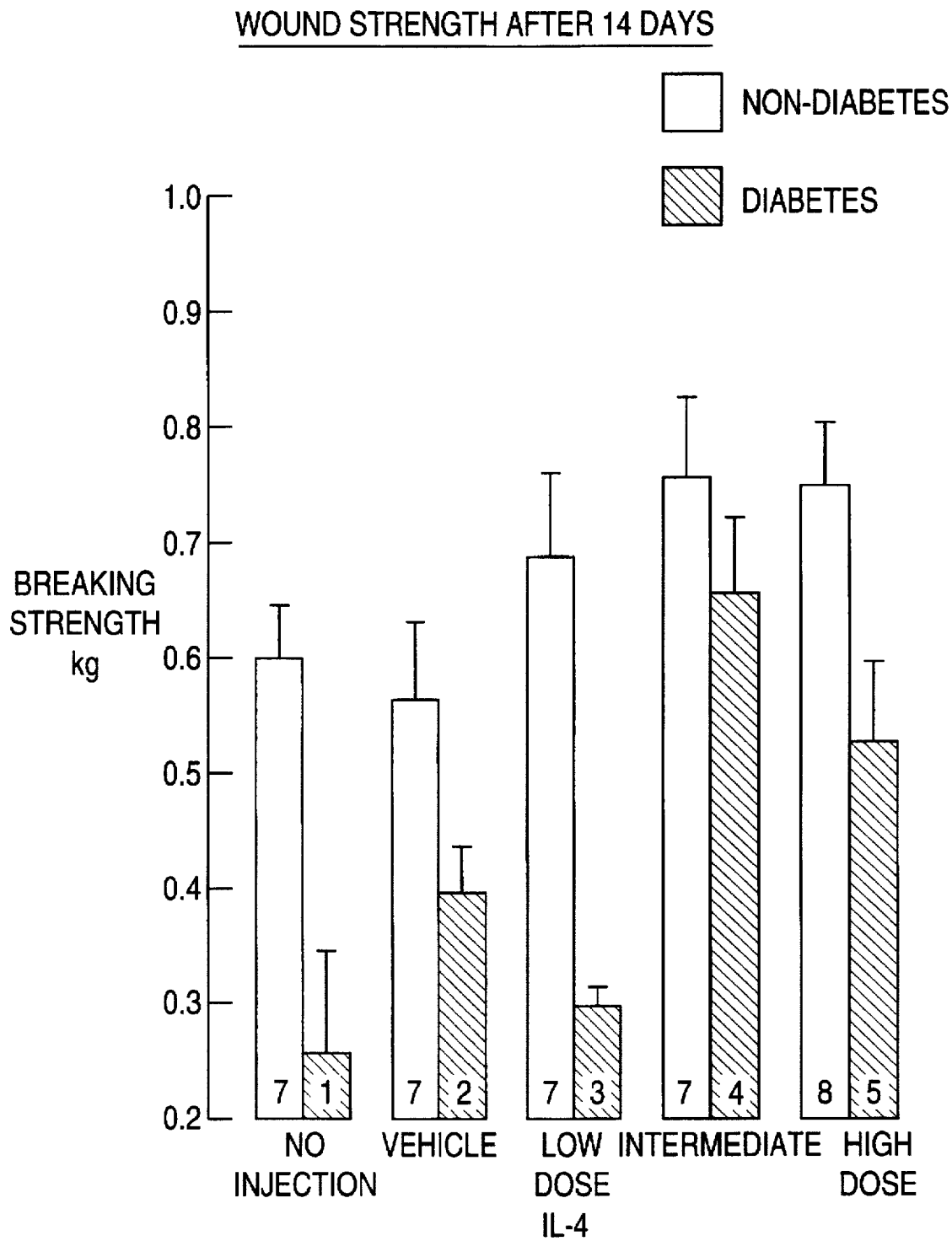
FIG. 12 is a graphic representation demonstrating the effectiveness of IL-4 in increasing the breaking strength of wounds in non-diabetic and diabetic animals at 14 days after wounding.

The data depicted FIGS. 11 & 12 demonstrate the effectiveness of IL-4 in increasing the breaking strength of wounds in non-diabetic and diabetic rats at 7 and 14 days respectively after wounding. As can be seen in the control graphs to the left, diabetic animals have an impairment in healing which results in a lower breaking strength of the wound. Treatment with IL-4 increases breaking strength in the diabetic animals close to the breaking strength of non-infected, non-diabetic, full thickness excisional wound.

What is claimed is:

1. A method of enhancing the reparative phase of wound healing and repair in a mammal in need of such enhancing which comprises administering during said reparative phase an amount of Interleukin-4 (IL-4) effective for such purpose.

2. The method of claim 1 wherein the IL-4 is administered topically at or in the vicinity of the wound site.

3. A method of enhancing the healing and repair of a wound of a mammal afflicted with diabetes mellitus which comprises administering to the wound of the mammal an amount of IL-4 effective for such purpose.

4. The method of claim 3 wherein the amount of IL-4 which is applied to the wound is from about 0.1 to about 15 micrograms of IL-4 per square centimeter of the wound.

5. A method of enhancing the healing and repair of an infected wound of a mammal which comprises administering to the infected wound of the mammal an amount of IL-4 effective for such purpose.

6. The method of claim 5 wherein the amount of IL-4 which is applied to the wound is from about 0.1 to about 15 micrograms of IL-4 per square centimeter of the wound.

7. A method of enhancing the healing and repair of a wound of an immunocompromised mammal which comprises administering to the wound of the mammal an amount of IL-4 effective for such purpose.

8. The method of claim 7 wherein the amount of IL-4 which is applied to the wound is from about 0.1 to about 15 micrograms of IL-4 per square centimeter of the wound.

9. A method for stimulating human fibroblast tissue cells during wound healing and repair, comprising the step of administering IL-4 in conjunction with a cytokine that possesses human fibroblast cell stimulatory activity, each in an amount effective for said stimulating.

10. The method of claim 9, wherein said cytokine is EGF.

11. The method of claim 9, wherein said cytokine is PDGF.

* * * * *